United States Patent [19]

Telfer et al.

[11] Patent Number: 5,262,549
[45] Date of Patent: Nov. 16, 1993

[54] BENZPYRYLIUM DYES, AND PROCESSES FOR THEIR PREPARATION AND USE

[75] Inventors: Stephen J. Telfer, Arlington; Socorro M. Ramos, Belmont; Michael J. Zuraw, Arlington, all of Mass.

[73] Assignee: Polaroid Corporation, Cambridge, Mass.

[21] Appl. No.: 39,696

[22] Filed: Mar. 29, 1993

Related U.S. Application Data

[63] Continuation of Ser. No. 708,048, May 30, 1991, abandoned.

[51] Int. Cl.$^5$ .................. C07D 311/58; C07D 413/14; C07D 405/14
[52] U.S. Cl. .................................. 549/404; 549/406; 549/408; 549/409; 549/218; 548/962; 548/950; 548/525; 548/454; 546/196; 544/151; 540/596; 540/480
[58] Field of Search ............... 549/219, 404, 406, 408, 549/409; 548/962, 950, 525, 454; 546/196; 544/151; 540/596, 480

[56] References Cited

U.S. PATENT DOCUMENTS

| | | | |
|---|---|---|---|
| 3,586,500 | 6/1971 | Contois et al. | 96/1.6 |
| 3,881,924 | 5/1975 | Murakami et al. | 96/1.6 |
| 3,896,112 | 7/1975 | Kubota | 260/240 D |
| 4,173,473 | 11/1979 | Petropoulos et al. | 430/72 |
| 4,233,443 | 11/1980 | Petropoulos et al. | 543/454 |
| 4,283,475 | 8/1981 | Kawamura et al. | 430/70 |
| 4,508,811 | 4/1985 | Gravesteijn et al. | 430/270 |
| 4,555,472 | 11/1985 | Katagiri et al. | 430/278 |
| 4,602,263 | 7/1986 | Borrer et al. | 346/201 |
| 4,663,260 | 5/1987 | Kitatani et al. | 430/83 |
| 4,714,667 | 12/1987 | Sato et al. | 430/270 |
| 4,720,449 | 1/1988 | Borrer et al. | 430/338 |
| 4,826,976 | 5/1989 | Borrer et al. | 544/58.4 |
| 4,857,431 | 8/1989 | Kato et al. | 430/91 |

FOREIGN PATENT DOCUMENTS

| | | |
|---|---|---|
| 1247915 | 3/1989 | Canada . |
| 3834960 | 5/1989 | Fed. Rep. of Germany . |
| 58-220143 | 12/1983 | Japan . |
| 61-167681 | 7/1986 | Japan . |
| WO88/04237 | 6/1988 | PCT Int'l Appl. . |

OTHER PUBLICATIONS

Kabuto et al., Bull. Chem. Soc. Japan, 46, 1839–1844 (1973).
Chemical Abstracts 81(19), 120,375v 1974 (Abstract of Vasserman et al., Khim. Geterotsiki. Soedin 7, 892–6, 1974).
Chemical Abstracts, 104(26), 234,392x (Abstract of Japanese Patent Application 84-108,441, Publication No. 60-252,346, published Dec. 13, 1985).
Von Strandtmann et al., J. Het. Chem., 9, 171 (1972).
Walter, W. and Proll, T., Synthesis, 1979, 941.
Luo, W. et al., Collect. Czech. Chem. Comm., 55, 2066 (1990).

*Primary Examiner*—Nicky Chan
*Attorney, Agent, or Firm*—David J. Cole

[57] ABSTRACT

4-[3-(benz[b]pyran-4-ylidene)prop-1-enyl]benz[b]pyrylium, 4-[5-(4H-benz[b]pyran-4-ylidene)penta-1,3-dienyl]benz[b]pyrylium and 4-[7-(4H-benz[b]pyran-4-ylidene)hepta-1,3,5-trienyl]benz[b]pyrylium dyes, wherein at least one of the benzpyrylium nuclei carries at its 2-position a substituent in which a non-aromatic carbon atom is bonded directly to the benzpyrylium nucleus, subject to the proviso that if the or each 2-substituent contains an aromatic nucleus, this aromatic nucleus is not conjugated with the benzpyrylium nucleus, are useful as visible and near infra-red absorbers, having high extinction coefficients and a reduced tendency to develop absorptions at shorter wavelengths when dispersed in polymeric media.

13 Claims, 7 Drawing Sheets

BENZPYRYLIUM DYES, AND PROCESSES FOR THEIR PREPARATION AND USE

This application is a continuation of application Ser. No. 07/708,048, filed May 30, 1991, now abandoned.

REFERENCE TO RELATED APPLICATION

The copending application Ser. No. 07/616,639, filed Nov. 21, 1990 by Stephen J. Telfer et al. and assigned to the same assignee as the present application, describes and claims certain chromones of Formula V (see FIG. 1 of the drawings accompanying the present application) used in the syntheses described and claimed in this application.

The copending application Ser. No. 07/616,982, filed Nov. 21, 1990 by K. C. Chang and assigned to the same assignee as the present application, describes and claims a thermal imaging medium having an abrasion-resistant overcoat, such as the overcoat 16 shown in FIG. 6 of the present application.

BACKGROUND OF THE INVENTION

This invention relates to 2-substituted 4-[3-(4H-benz[b]pyran-4-ylidene)prop-1-enyl]benz[b]pyrylium, 4-[5-(4H-benz[b]pyran-4-ylidene)penta-1,3-dienyl]-benz[b]pyrylium and 4-[7-(4H-benz[b]pyran-4-ylidene)-hepta-1,3,5-trienyl]benz[b]-pyrylium dyes, hereinafter for brevity referred to simply as "bisbenzpyrylium" dyes. This invention also relates to processes for the preparation of these dyes and processes for their use as visible or near infra-red absorbers.

The term "near infra-red" is used herein to mean electromagnetic radiation having a wavelength of about 700 to about 1200 nm.

Visible and near infra-red absorbers, that is to say compounds which absorb visible and/or near infra-red electromagnetic radiation, are known to be useful in a number of applications. For example, such absorbers are useful as filters used in photography and for protecting sensitive materials from visible and infra-red radiation, and in inks used to print characters intended to be read using visible or near infra-red light—for example, in universal product code labels intended to be scanned with an infra-red laser. Such absorbers are sometimes useful as sensitizers to render photographic film sensitive to red or near infra-red radiation, and some of them can act as charge transfer materials and are thus applied to the photosensitive surfaces used in xerography and in other types of electrophotography.

A wide variety of compounds have been used as visible and infra-red absorbers, including benzthiazoles, metal dithiolenes and phthalocyanines. Benzpyrylium and benzthiopyrylium dyes have also been used for this purpose.

For example, Canadian Patent No. 1,247,915 discloses a bis(4-benzpyrylium) pentamethine dye used as an infra-red sensitizer. The nuclei each carry a 2-phenyl substituent and a 7-acetyl group.

U.S. Pat. Nos. 4,173,473 and 4,233,443, disclose bis(4-pyrylium) and bis(4-benzpyrylium) trimethine compounds for use in radiation sensitive compositions; in these compounds, the trimethine chain is aryl-substituted.

U.S. Pat. No. 4,714,667, issued Dec. 22, 1987, describes an optical information recording medium comprising a recording layer on a substrate and an optional protective layer; the recording layer comprises a hexa-, penta-, tetra- or trimethine compound wherein three of the carbon atoms of the polymethine chain form part of a ring, and each end of the polymethine chain bears any one of a variety of heterocyclic groups, including benzpyrylium groups. The two specific compounds disclosed containing 4-benzpyrylium groups (compounds 11 and 27) both have 2-phenyl substituents.

U.S. Pat. No. 4,857,431, issued Aug. 15, 1989, describes a photoconductive composition comprising an inorganic photoconductive material, a sensitizing dye and a resin binder. The dye comprises a penta- or heptamethine compound wherein each end of the polymethine chain bears any one of a variety of heterocyclic groups, including benzpyrylium groups. These heterocyclic groups may bear alkyl and other substituents.

U.S. Pat. No. 4,283,475, issued August 11, 1981 describes 2,6-di-tert-butyl-4-[5-(2,6-di-tert-butyl-4H-thiopyran-4-ylidene)penta-1,3-dienyl]-thiopyrylium salts, which are colorless, transparent, have an adsorption in the far infrared to near infrared region and are capable of imparting high sensitivity to photoconductive substance; a process for producing the salts; and a photoconductive composition containing the salts.

Japanese Patent Application No. 103,604/82 (Publication No. 220,143/83, published Dec. 21, 1983), discloses a broad class of bis-heterocyclic pentamethine dyes in which the central three carbon atoms of the pentamethine chain form part of a squarylium or croconylium ring. The heterocyclic nuclei can be pyrylium, thiopyrylium, selenopyrylium, benzpyrylium, benzthiopyrylium, benzselenopyrylium, naphthopyrylium, naphthothiopyrylium or naphthoselenopyrylium nuclei, which can be substituted with alkyl, alkoxy, aryl or styryl groups.

Japanese Patent Application No. 60-8730 (Publication No. 167,681/86, published Jul. 29, 1986), discloses bis(4-benz[b]thiopyrylium pentamethine dyes in which the central three carbon atoms of the pentamethine chain for part of a squarylium ring. The dyes are intended for use as infra-red absorbers.

West German Offenlegungsschrift No. 38 34 960 discloses a bis(2-t-butyl-4-benzpyrylium) monomethine dye for use in a photopolymerizable composition.

Visible and infra-red absorbers have the capacity to absorb infra-red radiant energy and convert it to heat, thereby heating any medium in which the infra-red absorber is present, and several applications of such absorbers depend upon such generation of heat. Thus, visible and infra-red absorbers can be used to induce chemical or physical changes in the medium containing them, and such chemical or physical changes can be induced with an appropriate wavelength of light. For example, a layer of visible or infra-red absorber spread over a supporting plate can undergo visually perceptible physical distortions upon illumination by an infrared laser, so that the layer acts as an optical recording medium, as in a compact disc. For example, U.S. Pat. No. 4,508,811, issued Apr. 2, 1985, describes an optical recording element in which the recording layer comprises a bis(2,6-dialkyl) pyrylium or thiopyrylium squarylium salt.

U.S. Pat. No. 4,555,472 describes an optical recording member comprising a bis(2,6-diaryl-4-pyrylium) trimethine compound, in which the central carbon atom of the trimethine chain may bear an alkyl or aryl substituent.

U.S. Defensive Publication No. 889,023 describes bis(benzpyrylium) pentamethine and heptamethine dyes in which the benzpyrylium nuclei bear 2-phenyl, 7-acetoxy-2-(2,4-dimethoxyphenyl) and 7-acetoxy-2-phenyl substituents. These compounds are used as sensitizers in electrophotographic elements.

Such chemical and physical changes can also be used in thermal imaging; the highly localized heating produced by the absorber can be used to create a high resolution image. For example, U.S. Pat. No. 4,720,449, issued Jan. 19, 1988, describes a thermal imaging method which comprises heating imagewise a di- or triarylmethane compound possessing within its di- or triarylmethane structure an aryl group substituted in the ortho position to the meso carbon atom with a moiety ring-closed on the meso carbon atom directly through a nitrogen atom, which nitrogen atom is also bound to a group with a masked acyl substituent that undergoes fragmentation upon heating to liberate the acyl group for effecting intramolecular acylation of the nitrogen atom to form a new group in the ortho position, whereby the di- or triarylmethane compound is rendered colored in an imagewise pattern corresponding to the imagewise heating.

U.S. Pat. No. 4,602,263 and U.S. Pat. No. 4,826,976 both describe thermal imaging systems for optical recording and particularly for forming color images. This thermal imaging method relies upon the irreversible unimolecular fragmentation of one or more thermally unstable carbamate moieties of an organic compound to effect a visually discernible color shift from colorless to colored, from colored to colorless or from one color to another.

International Patent Application No. PCT/US87/03249 (Publication No. WO 88/04237), published Jun. 16, 1988, describes a different type of thermal imaging system using an element comprising a support formed of a material transparent to radiation of a specific wavelength and having an imaging surface layer heat activatable at an elevated temperature, and a layer of porous or particulate imaging material uniformly coated on the imaging surface layer and exhibiting a cohesive strength which is greater than the adhesive strength between the imaging material and the imaging surface layer. When this element is illuminated with radiation of the specific wavelength, at least one of the materials used in the two layers absorbs this radiation, thus heat activating the imaging surface layer and locking substantially the entire layer of the imaging material to the support when the imaging surface layer cools. After exposure of the element, a peeling force is applied to the imaging material so that in the unexposed areas of the element, the imaging material will peel from the support; however, in the exposed areas, the locking of the imaging material causes this material to be retained upon the support.

In many thermal imaging systems in which a leuco dye is transformed into a colored compound by heat, the leuco dye often does not have sufficient absorption at a convenient wavelength to permit it to convert sufficient radiation to heat to effect the color change. For example, in the forementioned U.S. Pat. Nos. 4,602,263 and 4,826,976, many of the leuco dyes absorb in the ultraviolet. In such thermal imaging systems, it is normally preferred to use a laser as the radiation source, and at present ultraviolet lasers are not well-suited to imaging processes, and such processes are preferably carried out using an infra-red laser. Accordingly, it is preferred to include with the leuco dye an infra-red absorber for converting infra-red radiation into heat, which is transferred to the leuco dye to effect the color change.

Similarly, in the thermal imaging system described in the aforementioned International Patent Application No. PCT/US87/03249, an infra-red absorber may be provided in a layer adjacent the imaging surface layer to assist in converting infra-red radiation into heat.

The requirements for visible and infra-red absorbers for use in thermal imaging systems are stringent. Since the sensitivity and the resolution of the image produced are often affected by the thickness of the layers in the heat-sensitive element (the sensitivity of the system is inversely related to the mass of material required to be heated, and thus inversely related to the thickness of the relevant layers), it is necessary to provide a high degree of absorption of radiation within a thin layer, sometimes of the order of 1 μm. To produce this degree of absorption, it is necessary that the absorber used have a high extinction coefficient, of the order of at least about 100,000, and a low molecular weight. In addition, in many cases it is desirable that the absorber manifest its maximum absorption within the range of about 700–1200 nm. so that it can conveniently be used with existing near infra-red lasers. (In the present state of technology, solid state diode lasers emitting at about 760 to 1000 nm. provide the highest output per unit cost. YAG lasers emitting at about 1000–1200 nm. are also useful in thermal imaging processes.)

One major problem with many prior art benzpyrylium dyes is that they have low solubility in most plastics and in the semi-polar solvents (for example, methyl ethyl ketone and methylene chloride) from which they need to be deposited to form imaging media such as those used in the aforementioned International Patent Application No. PCT/US87/03249. Thus, it is difficult to dissolve or disperse the absorber in a plastic without forming aggregates and without adversely affecting other properties of the plastic.

Accordingly, there is still a need for development of improved visible and near infra-red absorbers.

The aforementioned co-pending application Ser. No. 07/616,639, discloses that 4-[[3-[(benz[b]-4H-pyran-4-ylidene)methyl]-2-hydroxy-4-oxo-2-cyclobuten-1-ylidene]methyl]benz[b]pyrylium hydroxide inner salt dyes (i.e., bisbenzpyrylium pentamethine dyes in which the central three carbon atoms of the pentamethine chain form part of a squarylium nucleus) in which the benzpyrylium nuclei carry 2-phenyl substituents have very low solubilities in most plastics and in semi-polar solvents (for example, methyl ethyl ketone and methylene chloride) from which they need to be deposited to form many types of imaging media. The application states that the solubility of bisbenzpyrylium pentamethine dyes can be substantially improved by providing on at least one of the benzpyrylium nuclei, a 2-substituent in which a non-aromatic carbon atom is bonded directly to the benzpyrylium nucleus; preferably, at least one of the benzpyrylium nuclei should also bear a bulky 7-substituent which extends substantially out of the plane of the benzpyrylium nucleus.

The present inventors have found that bis(2-phenyl-benzpyrylium) dyes in which the two benzpyrylium nuclei are linked by a straight polymethine chain do not share the very low solubilities in plastics and semi-polar solvents of bis(2-phenyl-benzpyrylium) dyes in which the two benzpyrylium nuclei are linked by a polymethine chain containing a squarylium ring; the straight-chain dyes can readily be incorporated into polymeric media such as those in most imaging systems. However, the present inventors have found, although these straight-chain dyes can be incorporated into polymeric media, the spectral characteristics of the dyes in such media are undesirable in a thermal imaging system.

The infra-red spectrum of a typical straight-chain dye of this type shows only a single major peak in solution (hereinafter referred to as "the primary peak"). However, when the straight-chain dye is dispersed in a plastic, a second infra-red absorption (hereinafter referred to as "the secondary peak") occurs at a substantially shorter wavelength, and this shorter wavelength absorption is typically stronger than the longer wavelength absorption. The development of the secondary peak is accompanied by a dramatic reduction in absorption at the wavelength of the primary peak, and neither peak displays as high an absorption as does the dye in solution. The resultant diminution in maximum absorption is highly disadvantageous in imaging systems (for example, that described in the aforementioned International Patent Application No. PCT/US87/03249) in which it is necessary to absorb a substantial fraction of incident radiation in a very thin layer, of the order of 1 μm.

It has now been found that the tendency for bis(2-phenylbenzpyrylium) straight chain dyes to develop strong absorptions at shorter wavelengths (and thus to absorb over a wide range of wavelengths) when dispersed in plastic films can be substantially reduced by providing, on at least one of the benzpyrylium nuclei, a 2-substituent in which a non-aromatic carbon atom is bonded directly to the benzpyrylium nucleus.

SUMMARY OF THE INVENTION

Accordingly, this invention provides a bis(benz[b]pyrylium) polymethine dye selected from the group consisting of 4-[3-(4H-benz[b]pyran-4-ylidene)prop-1-enyl]benz[b]pyrylium dyes, 4-[5-(4H-benz[b]pyran-4-ylidene)penta-1,3-dienyl]benz[b]pyrylium dyes, and 4-[7-(4H-benz[b]pyran-4-ylidene)hepta-1,3,5-trienyl]-benz[b]pyrylium dyes, wherein at least one of the benzpyrylium nuclei carries at its 2-position a substituent in which a non-aromatic carbon atom is bonded directly to the benzpyrylium nucleus, subject to the proviso that if this 2-substituent contains an aromatic nucleus, this aromatic nucleus is not conjugated with the benzpyrylium nucleus. It should be noted that, in the dyes of the present invention, the or each 2-substituent may comprise a phenyl or other aromatic nucleus provided that this nucleus is separated from the benzpyrylium nucleus by at least one $sp^3$ carbon atom (or another saturated atom) so that the aromatic nucleus is not conjugated with the benzpyrylium nucleus.

Preferred 2-substituents include substituted and unsubstituted alkyl and cycloalkyl groups.

Preferred dyes of this invention are those wherein the bis(benzpyrylium) polymethine dye moiety is of the formula:

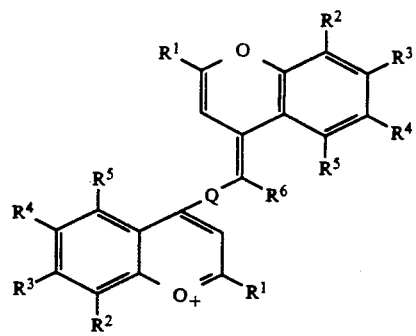

wherein:

Q is a group of formula $CR^6\!=\!CR^7$, $CR^6\!=\!CR^7\!-\!CR^8\!=\!CR^9$ or $CR^6\!=\!CR^7\!-\!CR^8\!=\!CR^9\!-\!CR^{10}\!=\!CR^{11}$;

each $R^1$ independently is an alkyl or cycloalkyl group which may be substituted or unsubstituted;

each $R^2$ and $R^4$ independently is a hydrogen atom, an alkyl group containing not more than about 8 carbon atoms or a halogen atom;

each $R^5$ independently is a hydrogen atom, an alkyl group containing not more than about 8 carbon atoms, a halogen atom, or an alkoxy group containing not more than about 12 carbon atoms;

each $R^3$ independently is a hydrogen atom, an alkyl group containing not more than about 8 carbon atoms, or a group in which an element of Group 5A, 6A or 7A is bonded directly to the benzpyrylium nucleus, subject to the proviso that when said element of Group 5A, 6A or 7A is at least divalent, $R^3$, together with one or both of $R^2$ and $R^4$ may comprise at least one saturated heterocyclic ring containing said element of Group 5A, 6A or 7A, this saturated heterocyclic ring optionally being fused to the benzene ring of the associated benzpyrylium nucleus;

each $R^6$ independently is a hydrogen atom or an alkyl group containing not more than about 6 carbon atoms;

each $R^7$, $R^8$, $R^9$, $R^{10}$ and $R^{11}$ independently is a hydrogen atom, an alkyl group containing not more than about 6 carbon atoms or a halogen atom, subject to the provisoes that:

when Q is a group $CR^6\!=\!CR^7\!-\!CR^8\!=\!CR^9$ $R^7$ and $R^9$ together, and when Q is a group $CR^6\!=\!CR^7\!-\!CR^8\!=\!CR^9\!-\!CR^{10}\!=\!CR^{11}$ at least one of $R^7$ and $R^9$ together, $R^8$ and $R^{10}$ together, and $R^9$ and $R^{11}$ together, may form a bridging group B such that the bridging group B and the three carbon atoms of the heptamethine chain lying between the ends of the bridging group form a cyclopentenyl ring, an alkyl-substituted cyclopentenyl ring, a cyclohexenyl ring, an alkyl-substituted cyclohexenyl ring, a benzcyclopentenyl ring or a benzcyclohexenyl ring; and when Q is a group $CR^6\!=\!CR^7\!-\!CR^8\!=\!CR^9\!-\!CR^{10}\!=\!CR^{11}$ $R^7$, $R^9$ and $R^{11}$ together may form a bridging group B' such that the bridging group B' and the five carbon atoms of the heptamethine chain lying between the ends of the bridging group form two cyclopentenyl and/or cyclohexenyl rings.

The dyes of the present invention may be cationic, anionic or non-ionic. When neither the polymethine chain nor either of the benzpyrylium nuclei carries any charged substituents, the bisbenzpyrylium polymethine moiety (hereinafter referred to simply as the "dye moiety") carries a single positive charge, and hence the dye is cationic and must have a negative counterion. However, if either the polymethine chain or either of the benzpyrylium nuclei carries a single negative group, the dye is non-ionic. Examples of such non-ionic dyes include those of Formula I above in which the heptamethine chain or either pyrylium ring carries a —COO$^-$ or —SO$_3^-$ group. Finally, if the polymethine chain and the benzpyrylium nuclei together carry two or more negative groups, the dye is anionic, and a positive counterion is required. In general cationic dyes of the present invention are preferred for solubility in semi-polar organic solvents and polymeric media.

This invention also provides a process for the preparation of a trimethine dye of the invention, which process comprises condensing two moles of a corresponding 4-alkylbenzpyrylium compound with a trialkyl orthoformate in the presence of a base.

This invention also provides a process for the preparation of a pentamethine dye of the invention, which process comprises condensing two moles of a corresponding 4-alkylbenzpyrylium compound with an acetal of the formula $(R^{12}O)_2CR^7$—$CHR^8$=$CR^9(OR^{12})$, wherein $R^7$, $R^8$ and $R^9$ are as defined above and $R^{12}$ is an alkyl group containing not more than about 6 carbon atoms, in the presence of a base and a dehydrating agent.

This invention also provides a process for the preparation of a pentamethine dye of the invention, which process comprises condensing the corresponding 4-alkylthiobenzpyrylium compound with the corresponding 4-(penta-1,3-dienyl)benzpyrylium compound.

This invention also provides a process for the preparation of a heptamethine dye of the invention, which process comprises condensing the corresponding 4-alkylbenzpyrylium compound or compounds with the corresponding glutaconaldehyde anil.

This invention also provides a process for the preparation of a heptamethine dye of the invention, which process comprises condensing two moles of the corresponding 4-alkylbenzpyrylium compound with a cyclopent-1-ene-1,3-dial in which the 2-carbon atom bears an electron-withdrawing substituent.

This invention also provides a process for generating heat in a medium comprising a dye of the invention, which process comprises exposing at least part of the medium to actinic radiation of a frequency absorbed by the dye, whereby the radiation is absorbed by the dye and heat is generated within the parts of the medium exposed to the radiation.

In one such process, the medium further comprises a thermally sensitive material capable of undergoing a color change upon exposure to heat, and the medium is exposed imagewise to the radiation, and the heat generated by the dye is sufficient to effect a color change in the thermally sensitive material, whereby an image is formed in the medium.

In a second such process, the medium comprises one layer of a multi-layer structure, this structure further comprising a support layer disposed on one side of the medium and a colored layer adhering to the opposed side of the medium, and wherein the heat generated on exposure of the dye to actinic radiation causes increased adhesion of the colored layer to the support layer, such that upon application of a peeling force to the colored layer, the colored layer will peel from the support layer in areas which have not been exposed to the radiation, but in areas which have been exposed to radiation the colored layer will remain attached to the support layer.

In a third such process, the heat generation causes a visually perceptible change in the medium so the medium forms an optical recording element.

Thus, this invention provides a recording element in which information can be recorded and read optically, which recording element comprises a supporting plate bearing a recording layer comprising a bisbenzpyrylium dye of the present invention.

(The term "image" is used herein to refer to any arrangement of areas which exhibit differing transmission and/or reflectance characteristics under electromagnetic radiation. Thus, the term "image" is used herein to include not only graphic or pictorial images but also textual material and quasi-textual material for machine "reading", for example bar codes.)

This invention also provides a 4-[1-alkylcyclohex-1-en-3-ylidenemethyl]benzpyrylium compound. These 4-[1-alkylcyclohex-1-en-3-ylidene-methyl]benzpyrylium compounds are useful as intermediates in the synthesis of the dyes of the present invention.

DETAILED DESCRIPTION OF THE INVENTION

Figure 1:
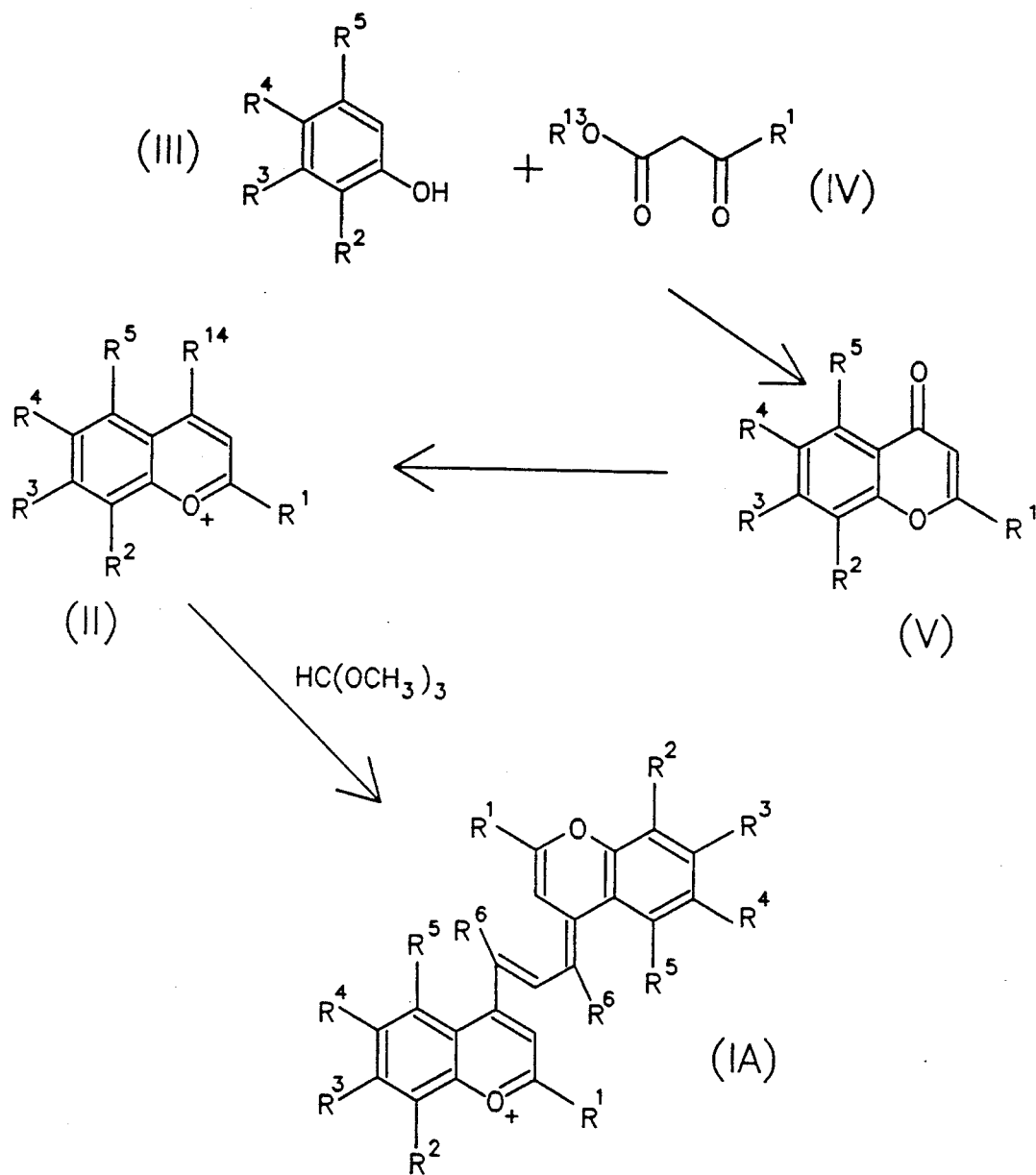
FIG. 1 of the accompanying drawings shows a first synthetic route used to produce a trimethine dye of the present invention.

As already mentioned, the present invention provides 4-[3-(4H-benz[b]pyran-4-ylidene)prop-1-enyl]benz[b]pyrylium, 4-[5-(4H-benz[b]pyran-4-ylidene)penta-1,3-dienyl]benz[b]pyrylium, and 4-[7-(4H-benz[b]pyran-4-ylidene)hepta-1,3,5-trienyl]benz[b]pyrylium dyes, wherein at least one of the benzpyrylium nuclei carries at its 2-position a substituent in which a non-aromatic carbon atom is bonded directly to the benzpyrylium nucleus (subject to the proviso that if this 2-substituent contains an aromatic nucleus, this aromatic nucleus is not conjugated with the benzpyrylium nucleus), these dyes being useful as visible and infra-red absorbers.

In the present dyes, the (or each) 2-substituent may have directly attached to the benzpyrylium nucleus, a non-aromatic sp, sp$^2$ or sp$^3$ carbon atom; for example, the or each 2-substituent could be a vinyl or ethine group. The (or each) 2-substituent can contain a phenyl or other aromatic nucleus provided that the aromatic nucleus is not conjugated with the benzpyrylium nucleus; thus, for example, a 3-phenylpropyl group can be used as the or each 2-substituent. However, as already noted, preferably the (or each) 2-substituent is a substituted or unsubstituted alkyl or cycloalkyl group. The 2-substituent could also comprise a saturated heterocyclyl group which is linked to the benzpyrylium nucleus by a carbon atom, for example a 2-piperidinyl or 2-morpholinyl group. It is desirable that the carbon atom of the or each 2-alkyl or cycloalkyl group which is directly attached to the benzpyrylium nucleus carry not more than one hydrogen atom, and preferably this carbon atom does not have any hydrogen atoms bonded directly thereto. α-Hydrogen atoms on the alkyl group are active hydrogens and may cause undesirable side reactions during the condensation used to produce the dye (as discussed in more detail below).

To reduce the shorter wavelength absorption when the dye is dispersed in a plastic, it is preferred that each of the benzpyrylium nuclei carry a substituted or unsubstituted 2-alkyl or cycloalkyl group. Although the 2-alkyl and cycloalkyl groups may bear various substituents, for example halogen atoms, for ease of synthesis it is generally preferred that the 2-alkyl and cycloalkyl groups be unsubstituted. Specific preferred 2-substituents are isopropyl, sec-butyl, tert-butyl, cyclohexyl, 2-tert-butylvinyl, 6,6-dimethylbicyclo-[3.1.1]hept-2-en-2-yl, bicyclo[2.2.1]hept-2-en-5-yl and adamantyl groups.

The benzpyrylium nuclei of the dyes of the present invention can bear a variety of substituents. The nature of the substituents $R^3$ may have substantial effects on the wavelength of maximum infra-red absorption ($\lambda_{max}$), as measured in dichloromethane, of the dye.

Desirably, at least one of the benzpyrylium nuclei carries at the 7-position a substituent in which an element of Group 5A, 6A or 7A of the Periodic Table is directly connected to the benzpyrylium nucleus, subject to the proviso that when this element of Group 5A, 6A or 7A is at least divalent, the 7-substituent may comprise at least one saturated heterocyclic ring containing the element of Group 5A, 6A or 7A, this saturated heterocyclic ring optionally being fused to the benzene ring of the associated benzpyrylium nucleus. For example, the 7-substituent may be a halogen atom. Preferred 7-substituents are alkoxy groups containing not more than about 12 carbon atoms, and disubstituted amino or disubstituted phosphino groups, wherein each of the substituents on the or each disubstituted group comprises an alkyl group containing not more than about 6 carbon atoms, or the two substituents on any one disubstituted group together form, with the nitrogen or phosphorus atom thereof, a heterocyclic ring system, this ring system optionally being fused to the benzpyrylium nucleus which carries the disubstituted amino or phosphino substituent.

Especially preferred are dyes in which each of the benzpyrylium nuclei carries a 7-disubstituted amino group. Disubstituted amino groups may be desirable to avoid the presence of active hydrogen atoms which might cause undesirable side-reactions in the condensation reactions used to prepare the present dyes, as discussed in more detail below. The substituents on the amino nitrogen may be two separate substituents, for example two separate alkyl groups, preferably alkyl groups containing not more than about 4 carbon atoms each, or phenyl groups. Alternatively, the two substituents together may form, with the nitrogen, a heterocyclic ring, for example a piperidine ring. Such a heterocyclic ring may contain an additional heteroatom (and thus, for example, the heterocyclic ring may be a morpholine ring), and/or be fused to another saturated or unsaturated ring; for example, the disubstituted amino group may be an indolinyl group. Finally, one or both of the substituents on the nitrogen may be divalent groups with their ends remote from the nitrogen attached to the benzpyrylium nucleus carrying the nitrogen, so that the disubstituted amino group becomes part of one or two heterocyclic rings fused to the benzpyrylium nucleus. For example, in the disubstituted amino group, one substituent could be a methyl group, while the other could be a trimethylene group having one end attached to a ring carbon ortho to the nitrogen atom, so that the nitrogen atom, the methyl group, the trimethylene group and two carbon atoms of the benzene ring form an N-methylpiperidino grouping fused to the benzene ring. Also, for example, the disubstituted amino group could be an —N[—(CH$_2$)$_3$—]$_2$ group in which the ends of the trimethylene groups remote from the nitrogen atom are joined to positions of the benzpyrylium nucleus ortho to the carbon atom carrying the nitrogen atom, so that the —N[—(CH$_2$)$_3$—]$_2$ group and the benzene ring of the benzpyrylium nucleus together form a julolidine ring system.

Disubstituted phosphino groups may bear all the types of substituents already discussed above with reference to disubstituted amino groups. Furthermore, the benzpyrylium nucleus may carry alkoxy substituents or modified alkoxy substituents in which one carbon atom is bonded to a phenyl carbon ortho to that carrying the oxygen atom, and the term "alkoxy" herein is to be construed accordingly. For example, one of the alkoxy groups could be an ethyleneoxy group having its β-carbon bonded to a phenyl carbon ortho to that carrying the oxygen atom, so that the ethyleneoxy group and two of the benzene carbons of the benzpyrylium nucleus form a dihydrofuran ring.

The benzpyrylium nuclei may also carry alkoxy groups at other than the 7-position; for example, each of the benzpyrylium nuclei could bear two alkoxy substituents at the 5- and 7-positions of each benzpyrylium nucleus.

The central polymethine chain of the dyes of the present invention may be unsubstituted, or may bear substituents, such as, for example, at least one halo, oxo or $C_1$–$C_{18}$ is alkyl substituent. Preferably, the carbon atoms α to the benzpyrylium nuclei are unsubstituted or carry alkyl groups containing from 1 to about 6 carbons atoms, desirably methyl groups. When the central polymethine chain is a pentamethine or heptamethine chain, the substituents on the carbon atoms β, γ and δ to the benzpyrylium nuclei may be in the form of bridging groups connected to the chain at two separate points so that the bridging group, together with the two carbon atoms in the chain to which it is attached and any intervening carbon atoms of the chain, forms a ring. Thus, for example, the bridging group may be an α,γ-dimethylene or -trimethylene bridge which forms, with three carbon atoms of the heptamethine chain, a cyclopentenyl or cyclohexenyl ring. The bridging group may also be an α,γ,ε-(CH$_2$)$_x$CH(CH$_2$)$_y$ group, in which x and y are each independently 1 or 2, so that the bridging group forms, with five carbon atoms of the heptamethine chain, two cyclopentenyl and/or cyclohexenyl rings. The rings formed by the bridging group may optionally be fused to benzene rings.

In general, the pentamethine and heptamethine dyes of the present invention are preferred over the trimethine dyes, since the pentamethine and heptamethine dyes (especially those having the preferred 7-substituents discussed above) have maximum absorptions at about 760-1000 nm in polymeric films; absorptions at these wavelengths are highly desirable with present infra-red lasers.

The counterion of the bisbenzpyrylium dye may be any counterion which is not incompatible with the dye moiety and which thus provides a stable salt. The choice of counterion may affect the tendency of the dye to exhibit lower wavelength absorption when dispersed in polymeric media. Preferred anions for cationic dyes of the present invention are tetrafluoroborate, trifluoromethyl sulfonate, tetraphenyl borate and hexafluorophosphate. It may often be found convenient, for synthetic reasons, to prepare a desired dye moiety with one counterion and thereafter to effect a counterion exchange to form a different salt of the same dye moiety.

The preferred group of dyes of Formula I have already been defined above, and the preferred values of the 2-substituent $R^1$ have already been described.

Unless $R^2$ and $R^4$ are required to form part of divalent substituents on an amino group, or part of an alkoxy group, both groups are conveniently hydrogen atoms, although either or both may be halogen atoms. Similarly, unless $R^5$ is an alkoxy group, it is conveniently a hydrogen atom, although $R^5$ may be a halogen atom.

In the dyes of Formula I, desirably each of the groups $R^3$ independently is:

(a) an alkoxy group containing not more than about 12 carbon atoms, or a disubstituted amino group wherein each of the substituents on the or each disubstituted group comprises an alkyl group containing not more than about 6 carbon atoms, or the two substituents on any one disubstituted group together form, with the nitrogen atom thereof, a saturated heterocyclic ring containing the nitrogen atom and optionally an oxygen atom, this saturated heterocyclic ring optionally being fused to one or two benzene rings;

(b) together with one of the groups $R^2$ and $R^4$ on the same benzene ring, a disubstituted amino group wherein one of the substituents comprises an alkyl group containing not more than about 6 carbon atoms and the other substituent comprises a polymethylene group, the end of the polymethylene group remote from the nitrogen atom being joined to the 6- or 8-position of the benzpyrylium nucleus carrying the nitrogen atom, so that the nitrogen atom, the polymethylene group, and two of the carbons of the benzpyrylium nucleus form a heterocyclic ring, the polymethylene group optionally being fused to an alicyclic or benzene ring; or (c) together with both the groups $R^2$ and $R^4$ on the same benzene ring, a disubstituted amino group wherein each of the substituents comprises a polymethylene group, the ends of the polymethylene groups remote from the nitrogen atom being joined to the 6- and 8-positions of the benzpyrylium nucleus carrying the nitrogen atom, so that the nitrogen atom, the two polymethylene groups, and three of the carbons of the benzpyrylium nucleus form two heterocyclic rings, one or both of the polymethylene groups optionally being fused to an alicyclic or benzene ring.

Preferably, each of the groups $R^3$ is a disubstituted amino group; specific preferred disubstituted amino groups are dimethylamino, diethylamino, piperidino, morpholino and indolinyl groups. Such disubstituted amino groups assist in providing high absorptions at about 800-960 nm in solution, and at slightly longer wavelengths in plastic films; absorptions at about these wavelengths are highly desirable with present infra-red lasers. Alternatively, when the $R^2$, $R^3$ and $R^4$ groups on the same ring together form a disubstituted amino group, this group is preferably an $-N[-(CH_2)_3-]_2$ group.

Although each group $R^6$ in Formula I may be, for example, an alkyl group containing not more than about 6 carbon atoms, in general for ease of synthesis it is preferred that each group $R^6$ be a hydrogen atom.

Specific preferred dyes of the present invention are those wherein:

a. Q is a group of formula $CR^6=CR^7-CR^8=CR^9$, $R^1$ is a tertiary butyl group, $R^3$ is a diethylamino group, and $R^2$, $R^4$, $R^5$, $R^6$, $R^7$, $R^8$ and $R^9$ are each a hydrogen atom, namely 4-[5-[7-diethylamino-2-[1,1-dimethylethyl]4H-benz[b]pyran-4-ylidene]penta-1,3-dienyl]-7-diethylamino-2-[1,1-dimethylethyl]benz[b]pyrylium salts;

b. Q is a group of formula $CR^6=CR^7-CR^8=CR^9$, $R^1$ is a tertiary butyl group, $R^3$ is an indolinyl group, and $R^2$, $R^4$, $R^5$, $R^6$, $R^7$, $R^8$ and $R^9$ are each a hydrogen atom, namely 4-[5-[7-indolinyl-2-[1,1-dimethylethyl]4H-benz[b]pyran-4-ylidene]penta-1,3-dienyl]-7-indolinyl-2-[1,1-dimethylethyl]benz[b]pyrylium salts;

c. Q is a group of formula $CR^6=CR^7-CR^8=CR^9$, $R^1$ is a tertiary butyl group, $R^3$ is a morpholino group, and $R^2$, $R^4$, $R^5$, $R^6$, $R^7$, $R^8$ and $R^9$ are each a hydrogen atom, namely 4-[5-[7-morpholino-2-[1,1-dimethylethyl]4H-benz[b]pyran-4-ylidene]penta-1,3-dienyl]-7-morpholino-2-[1,1-dimethylethyl]benz[b]pyrylium salts;

d. Q is a group of formula $CR^6=CR^7-CR^8=CR^9$, $R^1$ is a secondary butyl group, $R^3$ is a diethylamino group, and $R^2$, $R^4$, $R^5$, $R^6$, $R^7$, $R^8$ and $R^9$ are each a hydrogen atom, namely 4-[5-[7-diethylamino-2-[1-methylpropyl]4H-benz[b]pyran-4-ylidene]penta-1,3-dienyl]-7-diethylamino-2-[1-methylpropyl]-benz[b]pyrylium salts;

e. Q is a group of formula $CR^6=CR^7-CR^8=CR^9$, $R^1$ is an isopropyl group, $R^3$ is a diethylamino group, and $R^2$, $R^4$, $R^5$, $R^6$, $R^7$, $R^8$ and $R^9$ are each a hydrogen atom, namely 4-[5-[7-diethylamino-2-[1-methylethyl]-4H-benz[b]pyran-4-ylidene]penta-1,3-dienyl]-7-diethylamino-2-[1-methylethyl]benz[b]pyrylium salts;

f. Q is a group of formula $CR^6=CR^7-CR^8=CR^9$, $R^1$ is an cyclohexyl group, $R^3$ is a diethylamino group, and $R^2$, $R^4$, $R^5$, $R^6$, $R^7$, $R^8$ and $R^9$ are each a hydrogen atom, namely 4-[5-[2-cyclohexyl-7-diethylamino-4H-benz[b]pyran-4-ylidene]penta-1,3-dienyl]-2-cyclohexyl-7-diethylamino-benz[b]pyrylium salts;

g. Q is a group of formula $CR^6=CR^7-CR^8=CR^9$, $R^1$ is an tertiary group, $R^3$ is a diethylamino group, $R^7$ and $R^9$ together form a $CH_2-C(CH_3)_2-CH_2$ group, and $R^2$, $R^4$, $R^5$, $R^6$ and $R^8$ are each a hydrogen atom, namely 4-[[3-[2-[1,1-dimethylethyl]-7-diethylaminobenz-[b]-4H-pyran-4-ylidene]methyl]-1,1-dimethylcyclohex-3-en-5-ylidenemethyl]-2-[1,1-dimethylethyl]-7-diethylaminobenz[b]pyrylium salts;

h. Q is a group of formula $CR^6=CR^7-CR^8=CR^9-CR^{10}=CR^{11}$, $R^1$ is a tertiary butyl group, $R^3$ is a diethylamino group, and $R^2$, $R^4$, $R^5$, $R^6$, $R^7$, $R^8$, $R^9$, $R^{10}$ and $R^{11}$ are each a hydrogen atom, namely 4-[7-[7-diethylamino-2-[1,1-dimethylethyl]-4H-benz[b]pyran-4-ylidene]hepta-1,3,5-trienyl]-7-diethylamino-2-[1,1-dimethylethyl]-benz[b]pyrylium salts;

i. Q is a group of formula $CR^6=CR^7-CR^8=CR^9-CR^{10}=CR^{11}$, $R^1$ is a tertiary butyl group, $R^3$ is a diethylamino group, $R^8$ and $R^{10}$ together form an orthophenylene group, $R^9$ is a chlorine atom, and $R^2$, $R^4$, $R^5$, $R^6$, $R^7$ and $R^{11}$ are each a hydrogen atom, namely 4-[1-[2-chloro-3-[1-[7-diethylamino-2-[1,1-dimethylethyl]-4H-benz[b]pyran-4-ylidene]eth-2-ylidene]inden-1-yl]ethen-2-yl]-7-diethylamino-2-[1,1-dimethylethyl]-benz[b]pyrylium salts; and j. Q is a group of formula $CR^6=CR^7-CR^8=CR^9$, $R^1$ is a tertiary butyl group, $R^5$, $R^6$, $R^7$, $R^8$, $R^9$, $R^{10}$ and $R^{11}$ are each a hydrogen atom, and $R^2$, $R^3$ and $R^4$ together form an $-N[-(CH_2)_3-]_2$ group in which the ends of the trimethylene groups remote from the nitrogen atom are joined to the benzpyrylium nucleus, so that the $-N[-(CH_2)_3-]_2$ group and the benzene ring of the benzpyrylium nucleus together form a julolidine ring system, namely 9-[5-[11-[1,1-dimethylethyl]-2,3,6,7-tetrahydro-1H,5H-[1]benzopyrano-[6,7,8-ij]quinolizin-9-ylidene]penta-1,3-dienyl]-11-[1,1-dimethylethyl]-2,3,6,7-tetrahydro-1H,5H-[1]benzopyrano[6,7,8-ij]quinolizinium salts.

Various preferred processes for the preparation of the dyes of the invention have already been defined above. Conceptually, most of these processes are similar in that each comprises condensing, in the presence of a base, two moles of a corresponding 4-alkylbenzpyrylium compound (Formula II in FIG. 1) with an appropriate one, three or five carbon fragment to form respectively a trimethine, pentamethine or heptamethine dye of the invention. To form a trimethine dye, the single carbon fragment is conveniently supplied by an trialkyl orthoformate, for example trimethyl or triethyl orthoformate. To form a pentamethine dye, the three carbon fragment is conveniently supplied by an acetal of the formula $(R^{12}O)_2CR^7-CHR^8=CR^9(OR^{12})$, wherein $R^7$, $R^8$ and $R^9$ are as defined above and $R^{12}$ is an alkyl group containing not more than about 6 carbon atoms. This condensation is conveniently conducted using triethylamine as the base in solution in acetic anhydride (which acts as a dehydrating agent) at 0° C. to ambient temperature. Finally, to form a heptamethine dye, the five carbon fragment is conveniently supplied by an anil.

It will be appreciated that, in these condensation reactions, the 4-alkyl substituent on the benzpyrylium compound must contain one more carbon atom than the substituent $R^6$ desired in the final dye, since the α-carbon atom of the 4-alkyl substituent forms the α carbon atom of the polymethine chain in the final dye.

Where the polymethine chain is a pentamethine or heptamethine chain containing a bridging group, conveniently the appropriate bridging group is formed in the three- or five-carbon fragment before the condensation to form the dye, as described in more detail below.

FIG. 1 shows a synthetic route for preparing a trimethine dye of the invention from the corresponding substituted phenol (III), in which $R^2$, $R^3$, $R^4$, and $R^5$ are as defined above with reference to Formula I. This phenol is first condensed with the appropriate β-ketoester (IV), in which $R^1$ is as defined above with reference to Formula I and $R^{13}$ is conveniently an alkyl group, typically a methyl group, to produce a 4-ketobenz-4H-pyran or chromone (V). (The term "β-ketoester" is used herein to include any compound having a tautomer of the Formula IV, even though the compound normally exists wholly or partially in a different tautomer, such as an enol form.) This condensation may be effected by heating the two reactants together, typically at about 200° C. (The chromone (V) may also be prepared by the alternative route described below with reference to FIG. 2.) The chromone (V) is then treated with a alkyl Grignard reagent, for example methyl magnesium bromide, and then with a strong acid, for example fluoboric acid, to produce the corresponding 4-alkylbenzpyrylium salt (II), in which $R^{14}$ is an alkyl group.

The 4-alkylbenzpyrylium salt (II) will of course usually contain the counterion of the acid used to produce it. As already noted above, it may often be convenient to use one counterion during the synthesis of a dye of the invention and then effect counterion exchange to produce the desired counterion in the final dye. Thus, it is not usually necessary to change the counterion in the 4-alkylbenzpyrylium salt (II). However, if it is desired to store the salt (II) for a long period, it may be desirable to convert this salt to one with a different counterion; the necessary counterion exchange can be effected by conventional techniques which are well-known to those skilled in the synthesis of such salts.

The salt (II) is then condensed with trimethyl orthoformate (or some other trialkyl orthoformate) to produce the final trimethine dye of the invention, of Formula IA. This condensation is carried out in the presence of a base, and relies upon the fact that the 4-methyl hydrogens of the salt (II) are active hydrogen atoms which will condense with the central carbon atom of the orthoformate. It is because this condensation relies upon the active hydrogens on the salt (II) that it may be desirable to choose the substituents on the salt (II) so as to avoid the presence of additional active hydrogen atoms thereon; obviously, additional active hydrogen atoms on the salt (II) may cause undesirable side-reactions which will lower the yield of dye (IA).

Figure 2:
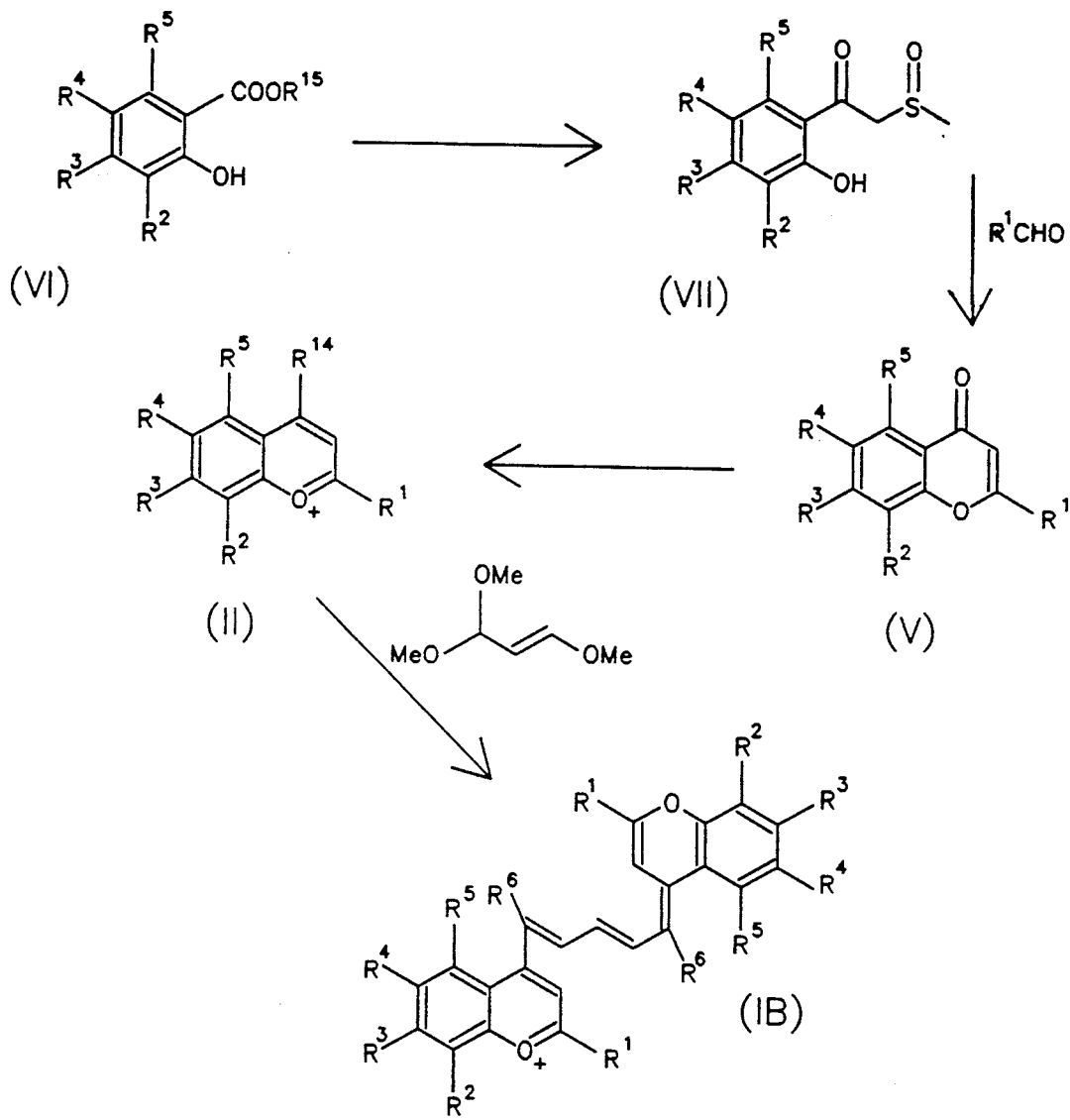
FIG. 2 shows a second synthetic route used to produce a pentamethine dye of the present invention.

In the synthesis of the pentamethine dye of the invention (IB) shown in FIG. 2, an alkyl salicylate (VI) (in which $R^{15}$ is typically an alkyl group containing not more than about 6 carbon atoms) is treated with dimethylsulfoxide in the presence of a strong base (sodium hydride being preferred) to produce a 2-$(CH_3-SO-CH_2-CO)$-phenol (VII). This phenol is then condensed with an aldehyde $R^1CHO$ to produce a chromone (V) identical to that shown in FIG. 1; if desired, this chromone (V) may be prepared by the route shown in FIG. 1. The chromone (V) is converted to the 4-alkylbenzpyrylium salt (II) in the same manner as described above. This salt (II) is then condensed with an acetal of the formula $(R^{12}O)_2CR^7-CHR^8=CR^9(OR^{12})$, wherein $R^7$, $R^8$ and $R^9$ are as defined above and $R^{12}$ is an alkyl group containing not more than about 6 carbon atoms (the compound in which $R^{12}$ is methyl and $R^7$, $R^8$ and $R^9$ are each a hydrogen atom is shown in FIG. 2), in the presence of a base and a dehydrating agent to yield the pentamethine dye of Formula IB.

Figure 3:
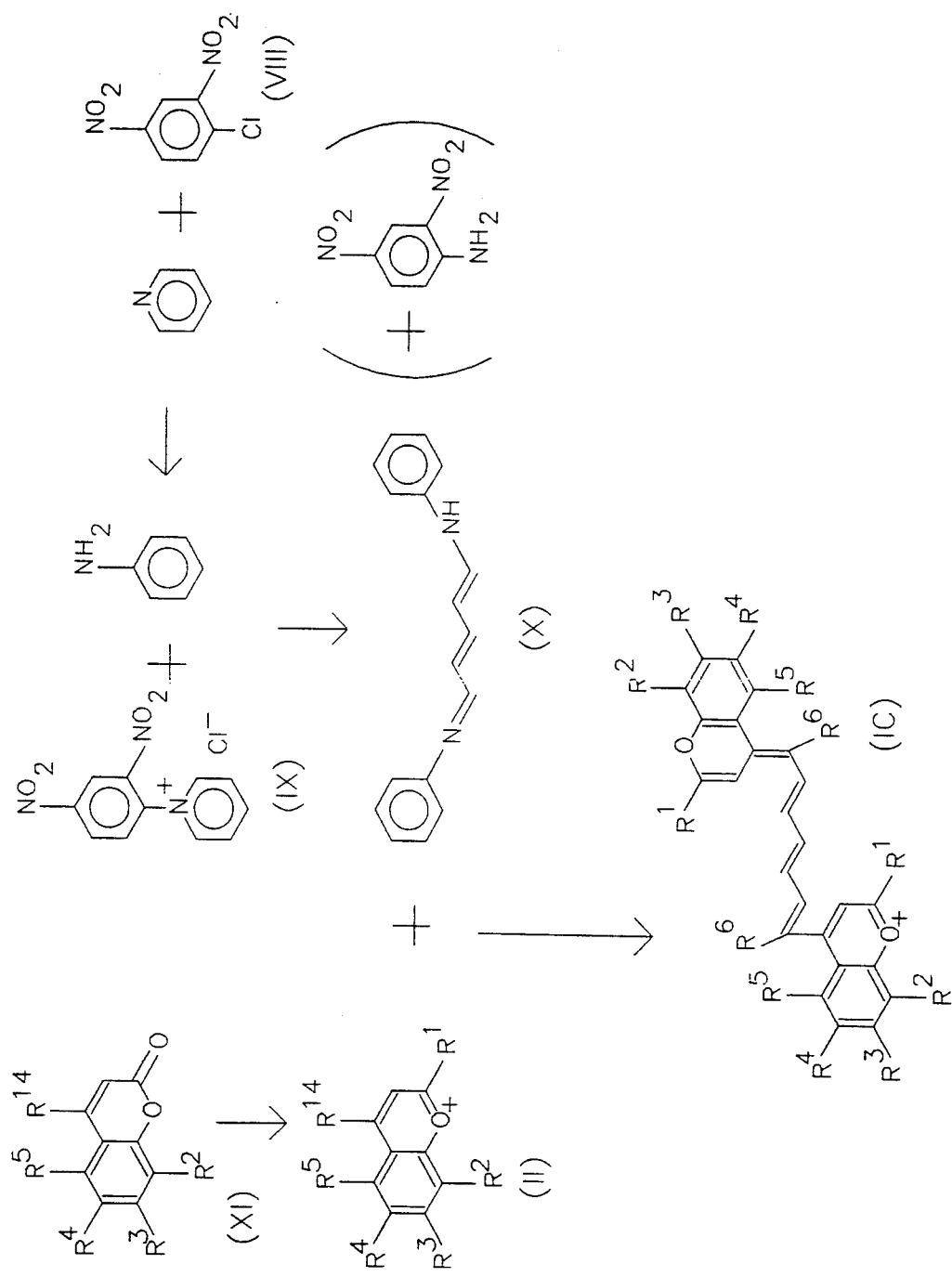
FIG. 3 shows a synthetic route used to produce a heptamethine dye of the present invention.

In the synthesis of the heptamethine dye of the invention (IC) shown in FIG. 3, 2,4-dinitrochlorobenzene (VIII) is treated with pyridine to yield N-(2,4-dinitrophenyl)pyridinium chloride (IX), which is then treated with aniline to give glutaconic dialdehyde dianil monohydrochloride (X) (for simplicity, this anil is shown in FIG. 3 in the form of the free base), 2,4-dinitroaniline being produced as a by-product.

FIG. 3 also shows a third synthetic route to the 4-alkylbenzpyrylium salt (II) which does not require first preparing a chromone (V). In the route shown in FIG. 3, the appropriate 4-alkyl-2-oxobenz-2H-pyran (XI), in which $R^{14}$ is as defined above, is reacted with an organometallic alkylating agent (preferably a Grignard reagent, for example t-butyl magnesium bromide) containing the desired substituent $R^1$ in a dialkoxyalkane, preferably dimethoxyethane, and then subjected to acid-mediated dehydration with, for example, fluoboric acid, to produce the 4-alkylbenzpyrylium salt (II).

In the final step of the synthesis, the anil (X) is condensed with the 4-alkylbenzpyrylium salt (II) to produce the heptamethine dye (IC).

Figure 4:
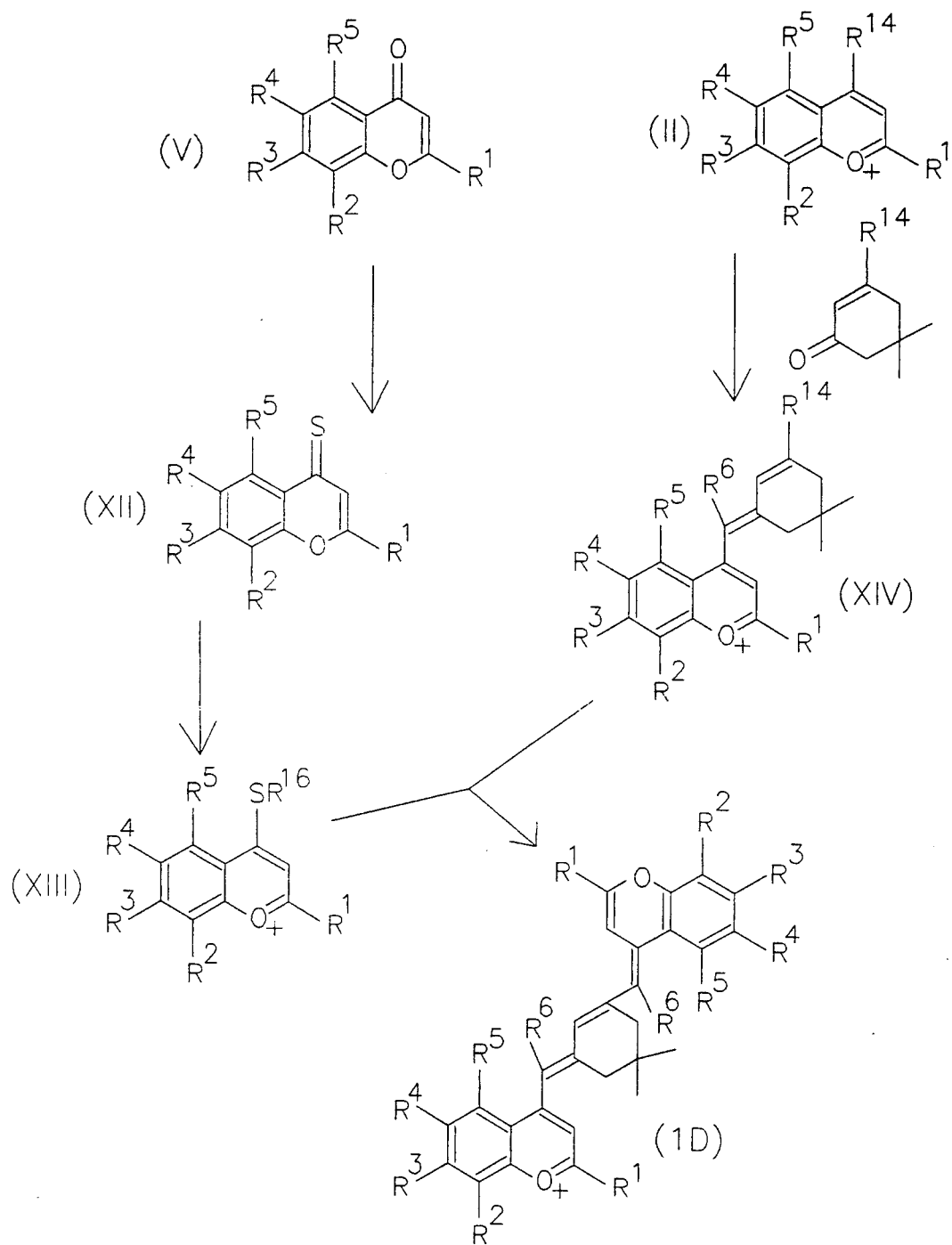
FIG. 4 shows a synthetic route used to produce a pentamethine dye of the present invention in which the central pentamethine chain contains a bridging group.

FIG. 4 shows the synthesis of a pentamethine dye (1D) of the invention; the pentamethine chain of this dye incorporates a 2,2-dimethyltrimethylene bridging group. This synthesis begins with the conversion of a chromone (V) to the corresponding 4-thione (XII); this conversion is conveniently effected using Lawesson's reagent. The thione (XII) is then treated with a trimethyloxonium salt, conveniently the tetrafluoroborate, to give the corresponding 4-thiomethoxy salt (XIII).

In a second branch of the synthesis, the appropriate 4-alkylbenzpyrylium salt (II) is condensed with the appropriate 3-alkylcyclohex-2-en-1-one derivative (in which $R^{14}$ is as defined above) to give the corresponding 4-(penta-1,3-dienyl)benzpyrylium compound (XIV). It should be noted that the groups $R^{14}$ on the two reactants need not be the same.

Finally, the 4-thiomethoxy salt (XIII) is condensed with the 4-(penta-1,3-dienyl)benzpyrylium compound (XIV) to give the pentamethine dye (1D). It will readily be apparent that this type of synthesis can be used to produce asymmetric dyes of the invention, that is dyes in which the two benzpyrylium nuclei are not the same. Furthermore, this type of synthesis can produce dyes in which the pentamethine chain is asymmetric; for example, the two groups $R^6$ in dye (1D) can be different.

Figure 5:
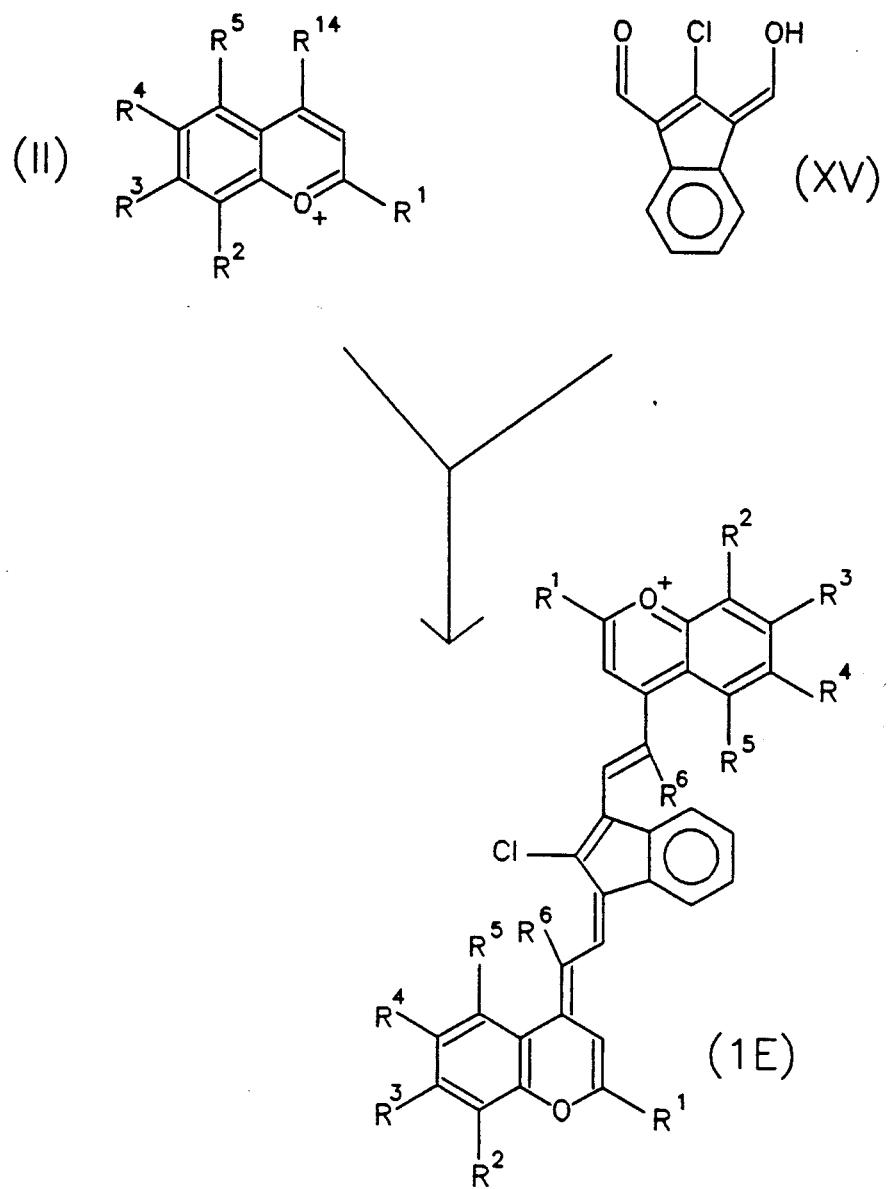
FIG. 5 shows a synthetic route used to produce a heptamethine dye of the present invention in which the central heptamethine chain contains a bridging group.

FIG. 5 shows the synthesis of a heptamethine dye (1E) of the invention; the heptamethine chain of this dye incorporates a benzcyclopentenyl bridging group. In this synthesis, two moles of the appropriate 4-alkylbenzpyrylium salt (II) are condensed with the appropriate pent-2-ene-1,5-dial (XV) (shown in its predominating mono-enol tautomer in FIG. 5) to produce the corresponding heptamethine dye (1E).

The dyes of the present invention may be used in any of the applications in which prior art visible and near infra-red absorbers have been used. Thus, the dyes may be used as dyes in printing inks intended to provide markings which can be read under visible or near infra-red radiation, for example, on packages of consumer items intended to be scanned by near infra-red laser scanners. At least some of the present dyes may also be useful as charge transfer materials for use in xerography, electrophotography and similar processes.

However, because of their high extinction coefficients in the visible or near infra-red region, the present dyes are especially useful in processes for generating heat in a medium; in such a process at least part of the medium is exposed to visible or (more usually) near infra-red actinic radiation of a frequency absorbed by the dye, so that the electromagnetic radiation is absorbed by the dye and heat is generated within the parts of the medium exposed to the radiation. Typically, in such a process, the radiation is provided by a laser. The medium may also comprise a thermally sensitive material capable of undergoing a color change upon exposure to heat; the medium is exposed imagewise to the radiation, and the heat generated by the dye is sufficient to effect a color change in the thermally sensitive material, so that an image is formed in the medium. Thus, for example, the present dyes may be used as the near infra-red absorbers in the thermal imaging processes described in the aforementioned U.S. Pat. Nos. 4,602,263 and 4,826,976.

In such a process, preferably the thermally sensitive material is originally substantially colorless and is converted by the heat generated to a colored material in exposed areas of the image.

Alternatively, the present dyes may be used in a thermal imaging process in which the medium comprises one layer of a multi-layer structure, this structure further comprising a support layer disposed on one side of the medium and a colored layer adhering to the opposed side of the medium. In this type of thermal imaging process, the heat generated on exposure of the dye to actinic radiation causes increased adhesion of the colored layer to the support layer, such that upon application of a peeling force to the colored layer, the colored layer will peel from the support layer in areas which have not been exposed to the radiation, but in areas which have been exposed to radiation the colored layer will remain attached to the support layer. A preferred thermal imaging process of this type is described and claimed in the aforementioned International Patent Application No. PCT/US87/03249.

In this type of thermal imaging process, desirably the support layer is formed of a material transparent to the radiation, and the colored layer comprises a layer of porous or particulate imaging material uniformly coated on the medium, the colored layer exhibiting a cohesive strength which is greater than the adhesive strength between the colored layer and the support layer. Preferably, the colored layer comprises carbon black, although other colored pigments or dyes may also be used.

Figure 6:
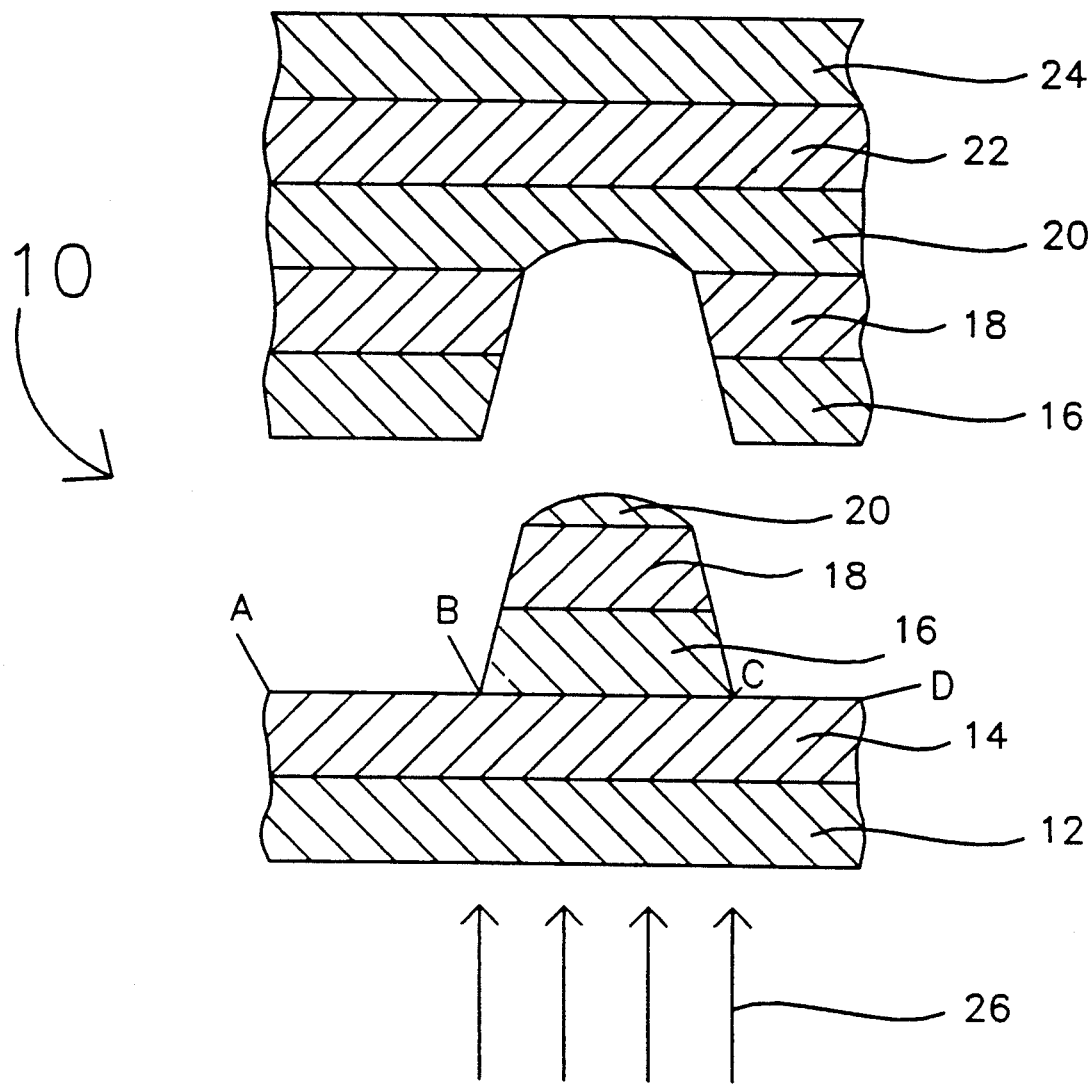
FIG. 6 is a schematic cross-section through a thermal recording medium used in a process of the present invention.

FIG. 6 is a schematic cross-section through a thermal recording medium used in this type of process of the present invention, this recording medium being shown in its exposed form with the two parts of the recording medium being separated to reveal the respective images. The thermal recording medium (generally designated 10) comprises a lower sheet 12 formed from a plastic film, preferably of polyethylene terephthalate, and carrying on its upper surface a sub-coat 14 formed of polystyrene or poly(styrene/acrylonitrile). (The thicknesses of the various layers are not drawn to scale in FIG. 6, the sub-coat being of course much thinner than the lower sheet 12). Above the sub-coat 14 are provided an overcoat 16 formed of an abrasion-resistant plastic, for example poly(methyl methacrylate) and a colorant/binder layer 18; this colorant/binder layer is preferably formed from a mixture of carbon black and polyvinyl alcohol.

A release layer 20 is provided above the colorant/binder layer 18, and an adhesive layer 22 above the release layer 20. Finally, a second sheet 24 formed from a plastic film, for example polyethylene terephthalate, completes the thermal recording medium 10.

The dye of the present invention may be incorporated in the sub-coat 14 or in the overcoat 16 or both. The dye serves to absorb near infra-red radiation from a laser which is used to expose the thermal recording medium and convert this radiation into heat, thereby raising the temperature of the interface between the sub-coat 14 and the overcoat 16; this interface constitutes the imaging surface of the thermal recording medium 10.

FIG. 6 shows the thermal recording medium being separated after it has been exposed using radiation from an infra-red laser. As indicated by the arrows 26, exposure has been effected such that the region from point B to point C is exposed, while the regions from point A to point B and from point C to point D are not exposed.

The various layers of the thermal recording medium 10 are chosen such that if in the unexposed medium the second sheet 24 is separated from the lower sheet 12, failure will occur at the imaging surface between the sub-coat 14 and the overcoat 16, so that all the colorant-/binder layer 18 will be a part of the image on the second sheet 24. However, when the medium 10 is exposed through the lower sheet 12, the heat which is generated adjacent the imaging surface in exposed regions (such as region BC in FIG. 6) causes increased adhesion of the overcoat 16 to the sub-coat 14. Accordingly, when the sheets 12 and 24 are separated, in such exposed regions failure occurs within the release layer 20. Thus, as shown in FIG. 6, at the boundaries between the exposed and unexposed regions, the failure line extends through the overcoat 16 and the colorant/binder layer 18, so that in the exposed regions the colorant/binder layer remains with the lower sheet 12.

Finally, the present dyes may also be used in a process in which the heat generated by exposure of the dye to radiation causes a visually perceptible change in the medium, so that the medium forms an optical recording element.

The bisbenzpyrylium dyes of the present invention are inherently stable and possess high extinction coefficients in the visible red or near infra-red regions; preferred dyes have strong absorptions at wavelengths which are convenient for use with present infra-red lasers. The dyes are readily soluble in semi-polar organic solvents and polymeric media, and can thus readily be incorporated into imaging media containing polymers. When dispersed in such polymeric media, the present dyes do not show the same tendency to develop strong absorptions at lower wavelengths as do the corresponding dyes which contain 2-phenylbenzpyrylium nuclei. The present dyes are believed to be of low toxicity and in general are substantially odor-free, in contrast to, for example, prior art thiopyrylium dyes, many of which have strong, objectionable smells. As explained above, the dyes can be synthesized in a small number of steps. The present dyes are of low molecular weight, and thus a high molar concentration of dye can be incorporated into polymeric media, thereby improving absorption of radiation as compared with other dyes having similar molar extinction coefficients but higher molecular weights. Moreover, straightforward modifications of the dyes of the invention allow tuning of physical properties, such as absorption wavelength and solubility in various media, in order to meet the needs of specific applications.

The following Examples are now given, though by way of illustration only, to show details of particularly preferred reagents, conditions and techniques used in the compositions and methods of the present invention.

EXAMPLE 1

Preparation of
7-diethylamino-2-(1,1-dimethylethyl)benz-4H-pyran-4-one

This Example illustrates the preparation, by the reaction shown in FIG. 1, of the chromone of Formula V in which $R^1$ is a tertiary butyl group, $R^3$ is a diethylamino group, and $R^2$, $R^4$ and $R^5$ are each a hydrogen atom.

3-Diethylaminophenol (5.0 g, 30.3 mmol) and methyl 4,4-dimethyl-3-oxopentanoate (5.0 g, 31.6 mmol) were heated together under nitrogen at 200° C. for 2 hours. The reaction mixture was cooled to room temperature, dissolved in dichloromethane and applied to a short column containing approximately 200 g of silica gel. The column was first eluted with dichloromethane to remove non-polar by-products, and subsequently eluted with ether to give 7-diethylamino-2-(1,1-dimethylethyl)benz-4H-pyran-4-one (2.7 g, 33% yield) as a brown oil. The structure of this compound was confirmed by mass spectroscopy and by $^1H$ and $^{13}C$ NMR spectroscopy; the $^{13}C$ NMR spectrum was: $\delta_c$ (75 Mhz in $CHCl_3$) 178.1, 174.4, 158.9, 151.8, 126.5, 112.5, 110.1, 105.8, 96.1, 44.6, 36.1, 27.8 and 12.4 ppm.

EXAMPLE 2

Preparation of
7-diethylamino-2-(1,1-dimethylethyl)benz-4H-pyran-4-one

This Example illustrates an improved version of the preparation of the same chromone as in Example 1 above.

3-Diethylaminophenol (500 g, 3.025 mol) and methyl 4,4-dimethyl-3-oxopentanoate (957 g, 6.05 mol) were stirred together at 180° C. under nitrogen with continuous removal of volatile reaction products for 36 hours. After this time, more methyl 4,4-dimethyl-3-oxopentanoate (47.85 g) was added and heating was continued for a further 3 hours. The reaction mixture was then cooled to room temperature and diluted with heptanes (4 L). The resultant solution was extracted with hydrochloric acid (0.5M, 6 L) and the aqueous layers were back-extracted with heptanes (4×2 L). The organic layers were combined, dried and concentrated in vacuo to give 7-diethylamino-2-(1,1-dimethylethyl)-benz-4H-pyran-4-one (673 g, 81% yield) as a brown oil which solidified upon standing. A small sample was further purified by silica gel chromatography and recrystallization from hexanes to give tan crystals which melted at 64.5°–65° C. The structure of this compound was confirmed by mass spectroscopy and by $^1H$ and $^{13}C$ NMR spectroscopy.

EXAMPLE 3

Preparation of
7-diethylamino-2-(1,1-dimethylethyl)benz-4H-pyran-4-one

This Example illustrates the preparation, by the reactions shown in FIG. 2, of the same chromone of Formula V as in Example 1 above.

PART A

Preparation of
4-dimethylamino-2-hydroxy-2'-(methylsulfonyl)acetophenone

This Part illustrates the preparation of the methylsulfonyl compound of Formula VII in which $R^3$ is a diethylamino group, and $R^2$, $R^4$ and $R^5$ are each a hydrogen atom. The procedure followed is analogous to that described in Von Strandtmann et al., J. Het. Chem., 9, 171 (1972).

Sodium hydride (2 g of a 50% dispersion in mineral oil, 0.042 mol) was added to dry dimethyl sulfoxide (25 mL). The resultant mixture was stirred at 60°–70° C. under nitrogen until hydrogen evolution ceased (approximately 1 hour). The solution was then cooled to 50° C. and a solution of methyl 4-diethylaminosalicylate (2.23 g, 0.01 mol) in toluene (25 mL) was added over a period of 5 minutes. The resultant solution was stirred at 40°–50° C. for 3 hours, then cooled to 20° C. and allowed to stand for 17 hours. The mixture was then poured into ice/water (150 mL) containing conc. hydrochloric acid (5 mL). Toluene (25 mL) was added and the mixture was extracted. The toluene layer was separated, washed with brine, dried over sodium sulfate and evaporated to afford the crude product as a yellow oil. Trituration with ether produced purified 4-dimethylamino-2-hydroxy-2'-(methylsulfonyl)-acetophenone (1.6 g, 59% yield) as a waxy brown solid, m.p. 91°–92° C. The structure of this compound was confirmed by mass spectroscopy and by $^1$H and $^{13}$C NMR spectroscopy.

PART B

Preparation of chromone

Piperidine (5 drops) was added to a solution of 4-dimethylamino-2-hydroxy-2'-(methylsulfonyl)acetophenone (0.25 g, 0.93 mmol) and trimethylacetaldehyde (0.1 g, 1.2 mmol) in toluene (50 mL). The resultant clear solution was heated at reflux for 18 hours, after which more piperidine (20 drops) was added and heating was continued for a further 24 hours. The tan solution was poured into water (50 mL) containing conc. hydrochloric acid (1 mL) and the resultant mixture extracted with toluene. The organic layer was separated, washed with brine, dried over sodium sulfate and evaporated to afford the crude product (0.14 g) as a brown oil. Mass spectroscopy and $^1$H and $^{13}$C NMR spectroscopy showed that the product contained the same chromone as prepared in Example 1 above.

EXAMPLE 4

Preparation of 7-diethylamino-2-(1,1-dimethylethyl)-4-methylbenzpyrylium tetrafluoroborate This Example illustrates the preparation, by the reaction shown in FIG. 1, of the tetrafluoroborate salt of Formula II in which $R^1$ is a tertiary butyl group, $R^3$ is a diethylamino group, $R^{14}$ is a methyl group, and $R^2$, $R^4$ and $R^5$ are each a hydrogen atom.

Methyl magnesium bromide (15.0 mL of a 3.0M solution in ether, 45 mmol) was added dropwise to a solution of 7-diethylamino-2-(1,1-dimethylethyl)benz-4H-pyran-4-one (7.9 g, 29 mmol, prepared in Example 1 above) in dry tetrahydrofuran (100 mL) at 0° C. under nitrogen. The reaction mixture was stirred at 25° C. for 64 hours; repetitions of the procedure indicated that only 17 hours was required for complete reaction. The reaction mixture was poured into a saturated ammonium chloride solution and the resultant mixture was extracted with dichloromethane. The organic layer was separated, dried over magnesium sulfate and evaporated. The residue was dissolved in methanol (30 mL) and tetrafluoroboric acid (4 mL of a 50% solution in water) was added. The solvents were removed and the residue was triturated with ether (4×50 mL). Evaporation of residual solvent in vacuo yielded 7-diethylamino-2-(1,1-dimethylethyl)-4-methylbenzpyrylium tetrafluoroborate (8.5 g, 82% yield) as a yellow foam. The structure of this compound was confirmed by mass spectroscopy and by $^1$H and $^{13}$C NMR spectroscopy; the $^{13}$C NMR spectrum was: $\delta_c$ (75 MHz in CHCl$_3$) 179.9, 164.1, 159.8, 156.5, 129.3, 118.4, 117.5, 111.3, 95.3, 46.2, 37.9, 28.2, 27.4 and 19.9 ppm.

EXAMPLE 5

Preparation of 7-diethylamino-2-(1,1-dimethylethyl)-4-methylbenzpyrylium tetrafluoroborate This Example illustrates an improved version of the preparation of the same salt as in Example 4 above.

Methyl magnesium bromide (40 mL of a 3M solution in ether, 0.12 mol) was added dropwise to a solution of 7-diethylamino-2-(1,1-dimethylethyl)-benz-4H-pyran-4-one (24.52 g, 0.0897 mol) in dry tetrahydrofuran (240 mL) at 0° C. under nitrogen. The reaction mixture was stirred at 25° C. for 17 hours, whereupon a further amount of methyl magnesium bromide (6 mL of a 3M solution in ether, 0.018 mol) was added. The resultant mixture was stirred at 25° C. for another four hours, then poured into water. Tetrafluoroboric acid (50 mL of a 48% solution in water) was added, and the mixture was extracted with dichloromethane. The resultant solution was dried over sodium sulfate and partially evaporated. Ethyl acetate was added and the remaining dichloromethane was removed. Filtration and drying afforded 7-diethylamino-2-(1,1-dimethylethyl)-4-methylbenzpyrylium tetrafluoroborate (25.33 g, 79% yield) as orange crystals which melted at 161° C. The structure of this compound was confirmed by mass spectroscopy and by $^1$H and $^{13}$C NMR spectroscopy.

EXAMPLE 6

Preparation of 7-diethylamino-2-(1,1-dimethylethyl)-4-methylbenzpyrylium tetrafluoroborate This Example illustrates the preparation, by the reaction shown in FIG. 3, of the same salt of Formula II as in Example 4 above but starting from the corresponding 4-methylcoumarin.

A solution of 7-diethylamino-4-methylcoumarin (2.3 g, 10 mmol) in dimethoxyethane (20 mL) was added dropwise at 25° C. to a vigorously stirred 2.0M solution of t-butyl magnesium chloride in tetrahydrofuran (10 mL). After the addition had been completed, the resultant mixture was stirred for 12 hours at ambient temperature, then poured into saturated ammonium chloride solution (100 mL) and the mixture was extracted twice with 100 mL aliquots of dichloromethane. The organic extracts were combined, dried over magnesium sulfate and evaporated to a volume of approximately 10 mL. The concentrate thus produced was diluted with ether (100 mL), and tetrafluoroboric acid (7 mL of a 50–52% solution in ether) was added immediately, causing separation of a black oil. The supernatant liquor was decanted and the residue washed with several portions of ether, then pumped under high vacuum overnight to give 4.1 g of a partially solidified black residue. Silica gel thin layer chromatography of this residue, eluting with 10% methanol in dichloromethane, showed a band at R$_f$ 0.3, which co-eluted with the salt produced in Example 4 above. Ultra-violet and visible spectroscopy further confirmed the identity of the product with the salt produced in Example 4 above, and indicated a yield of 24% based upon the coumarin starting material.

EXAMPLE 7

Preparation of
4-[5-[7-diethylamino-2-[1,1-dimethylethyl]4H-benz[b]-pyran-4-ylidene]penta-1,3-dienyl]-7-diethylamino-2-[1,1-dimethylethyl]benz[b]pyrylium tetrafluoroborate This Example illustrates the preparation, by the reaction shown in FIG. 2, one of the dye of Formula IB in which $R^1$ is a tertiary butyl group, $R^3$ is a diethylamino group, and $R^2$, $R^4$, $R^5$ and $R^6$ are each a hydrogen atom.

Triethylamine (2.0 g, 0.48 mol) was added dropwise to a solution of 7-diethylamino-2-(1,1-dimethylethyl)-4-methylbenzpyrylium tetrafluoroborate (4.966 g, 13.8 mmol, prepared in Example 5 above) and 1,3,3-trimethoxy-1-propene (0.918 g, 6.95 mmol) in acetic anhydride (70 mL) with ice-bath cooling under nitrogen. The reaction mixture was allowed to stand at room temperature for 1 hour, and then poured into hexanes (100 mL). The resultant two-phase mixture was separated and the hexane layer was discarded. The material remaining was triturated with ether and dissolved in the minimum amount of dichloromethane. Heptane was added to precipitate the dye, which was redissolved in dichloromethane and washed with water. The organic layer was dried over sodium sulfate and concentrated in vacuo to give the dye as a violet solid (3.09 g, 67% yield). The dye had a strong infra-red absorption at 828 nm in dichloromethane solution, $\epsilon=331,000$. The structure of this compound was confirmed by mass spectroscopy and by $^1H$ and $^{13}C$ NMR spectroscopy.

EXAMPLE 8

Preparation of
7-indolinyl-2-(1,1-dimethylethyl)1benz-4H-pyran-4-one

This Example illustrates the preparation, by the reaction shown in FIG. 1, of the chromone of Formula V in which $R^1$ is a tertiary butyl group, $R^3$ is an indolinyl group, and $R^2$, $R^4$ and $R^5$ are each a hydrogen atom.

3-Indolinylphenol (2.9 g, 14.5 mmol) and methyl 4,4-dimethyl-3-oxopentanoate (2.5 g, 15.8 mmol) were heated together under nitrogen at 200° C. for 2 hours. The reaction mixture was cooled to room temperature, dissolved in dichloromethane and applied to a short column containing approximately 100 g of silica gel. The column was first eluted with dichloromethane to remove non-polar by-products, and subsequently eluted with ether to give 7-indolinyl-2-(1,1-dimethylethyl)benz-4H-pyran-4-one (1.2 g, 26% yield) as a yellow oil. The structure of this compound was confirmed by mass spectroscopy and by $^1H$ and $^{13}C$ NMR spectroscopy.

EXAMPLE 9

Preparation of
7-indolinyl-2-(1,1-dimethylethyl)-4-methylbenzpyrylium tetrafluoroborate This Example illustrates the preparation, by the reaction shown in FIG. 1, of the tetrafluoroborate salt of Formula II in which $R^1$ is a tertiary butyl group, $R^3$ is an indolinyl group, $R^{14}$ is a methyl group, and $R^2$, $R^4$ and $R^5$ are each a hydrogen atom.

Methyl magnesium bromide (1 mL of a 3.0M solution in ether, 3 mmol) was added dropwise to a solution of 7-indolinyl-2-(1,1-dimethylethyl)benz-4H-pyran-4-one (220 mg, 0.69 mmol, prepared in Example 8 above) in dry tetrahydrofuran (10 mL) at 0° C. under nitrogen, and the resultant solution was stirred at 25° C. for 17 hours, after which time tetrafluoroboric acid (1.5 mL of a 48% solution in water) was added, and the mixture was diluted with water and extracted with dichloromethane. The organic extracts were dried over magnesium sulfate and concentrated in vacuo. Ether was added and the solid formed was collected by vacuum filtration and washed with more ether to give 7-indolinyl-2-(1,1-dimethylethyl)-4-methylbenzpyrylium tetrafluoroborate (203 mg, 73% yield) as purple crystals which melted at 257°-264° C. with decomposition. The structure of this compound was confirmed by mass spectroscopy and by $^1H$ and $^{13}C$ NMR spectroscopy.

EXAMPLE 10

Preparation of
4-5-7-indolinyl-2-[1,1-dimethylethyl]4H-benz[b]pyran-4-ylidene]penta-1,3-dienyl]-7-indolinyl-2-[1,1-dimethylethyl]benz[b]pyrylium tetrafluoroborate This Example illustrates the preparation, by the reaction shown in FIG. 2, of the dye of Formula IB in which $R^1$ is a tertiary butyl group, $R^3$ is an indolinyl group, and $R^2$, $R^4$, $R^5$ and $R^6$ are each a hydrogen atom.

Triethylamine (25 mg, 0.24 mmol) was added dropwise at room temperature to a solution of 7-indolinyl-2-(1,1-dimethylethyl)-4-methylbenzpyrylium tetrafluoroborate (100 mg, 0.25 mmol, prepared in Example 9 above) and trimethoxyprop-1-ene (20 mg, 0.17 mmol) in acetic anhydride (5 mL) and the reaction mixture was allowed to stand for 4 hours. After this time, hexane (20 mL) and ether (20 mL) were added to precipitate the crude dye. After removal of the solvents by decantation, the crude product was dissolved in dichloromethane and washed with water. The resultant solution was dried over magnesium sulfate and concentrated in vacuo to give the dye as a black powder (31 mg, 33% yield). The dye had a strong infra-red absorption at 854 nm in dichloromethane solution, $\epsilon=120,000$. The structure of this compound was confirmed by mass spectroscopy and by $^1H$ and $^{13}C$ NMR spectroscopy.

EXAMPLE 11

Preparation of
7-morpholino-2-(1,1-dimethylethyl)benz-4H-pyran-4-one

This Example illustrates the preparation, by the reaction shown in FIG. 1, of the chromone of Formula V in which $R^1$ is a tertiary butyl group, $R^3$ is an morpholino group, and $R^2$, $R^4$ and $R^5$ are each a hydrogen atom.

3-Morpholinophenol (15.0 g, 84 mmol) and methyl 4,4-dimethyl-3-oxopentanoate (15 g, 95 mmol) were heated together under nitrogen at 200° C. for 12 hours. The reaction mixture was cooled to room temperature, dissolved in dichloromethane and the resulting solution (200 mL) was washed sequentially with 1M sodium hydroxide and water. The organic layer was then separated and dried over magnesium sulfate. The solvent was evaporated and the residue applied to a short column containing approximately 400 g of silica gel. The column was first eluted with dichloromethane to remove non-polar by-products, and subsequently eluted with ether to give 7-morpholino-2-(1,1-dimethylethyl)benz-4H-pyran-4-one (6.72 g, 28% yield) as a yellow oil. The structure of this compound was confirmed by mass spectroscopy and by $^1H$ and $^{13}C$ NMR spectroscopy.

EXAMPLE 12

Preparation of
7-moroholino-2-(1,1-dimethylethyl)-4-methylbenzpyrylium tetrafluoroborate This Example illustrates the preparation, by the reaction shown in FIG. 1, of the tetrafluoroborate salt of Formula II in which $R^1$ is a tertiary butyl group, $R^3$ is an morpholino group, $R^{14}$ is a methyl group, and $R^2$, $R^4$ and $R^5$ are each a hydrogen atom.

Methyl magnesium bromide (5 mL of a 3.0M solution in ether, 15 mmol) was added dropwise to a solution of 7-morpholino-2-(1,1-dimethylethyl)benz-4H-pyran-4-one (2.87 g, 10 mmol, prepared in Example 11 above) in dry tetrahydrofuran (20 mL) at 0° C. under nitrogen, and the solution was stirred at 25° C. for 17 hours, after which time tetrafluoroboric acid (7 mL of a 48% solution in water) was added, and the mixture was diluted with water and extracted with dichloromethane. The organic extracts were dried over magnesium sulfate and concentrated in vacuo. The solid formed was triturated with ether until it solidified and was then collected by vacuum filtration and washed with more ether to give 7-morpholino-2-(1,1-dimethylethyl)-4-methylbenzpyrylium tetrafluoroborate (2.24 g, 60% yield) as an orange powder which melted at 160°-163° C. The structure of this compound was confirmed by mass spectroscopy and by $^1H$ and $^{13}C$ NMR spectroscopy.

EXAMPLE 13

Preparation of
4-[5-[7-morpholino-2-[1,1-dimethylethyl]4H-benz[b]pyran-4-ylidenelpenta-1,3-dienyl]-7-morpholino-2-[1,1-dimethylethyl]benz[b]pyrylium tetrafluoroborate This Example illustrates the preparation, by the reaction shown in FIG. 2, of the dye of Formula IB in which $R^1$ is a tertiary butyl group, $R^3$ is an morpholino group, and $R^2$, $R^4$, $R^5$ and $R^6$ are each a hydrogen atom.

Triethylamine (303 mg, 3 mmol) was added dropwise at room temperature to a solution of 7-morpholino-2-(1,1-dimethylethyl)-4-methylbenzpyrylium tetrafluoroborate (1.0 g, 2.7 mmol, prepared in Example 12 above) and trimethoxyprop-1-ene (20 mg, 2.7 mmol) in acetic anhydride (20 mL) and the reaction mixture was allowed to stand for 4 hours. After this time, hexane (100 mL) and ether (100 mL) were added to precipitate the crude dye. After removal of the solvents by decantation, the crude product was dissolved in dichloromethane and washed with water. The resultant solution was dried over magnesium sulfate and concentrated in vacuo to give the dye as green crystals (624 mg, 67% yield). The dye had a strong infra-red absorption at 809 nm in dichloromethane solution, $\epsilon=260,000$. The structure of this compound was confirmed by mass spectroscopy and by $^1H$ and $^{13}C$ NMR spectroscopy.

EXAMPLE 14

Preparation of
7-piperidino-2-(1,1-dimethylethyl)benz-4H-pyran-4-one

This Example illustrates the preparation, by the reaction shown in FIG. 1, of the chromone of Formula V in which $R^1$ is a tertiary butyl group, $R^3$ is a piperidino group, and $R^2$, $R^4$ and $R^5$ are each a hydrogen atom.

3-Piperidinophenol (1.0 g, 5.7 mmol) and methyl 4,4-dimethyl-3-oxopentanoate (1.0 g, 6.3 mmol) were heated together under nitrogen at 200° C. for 5 hours. The reaction mixture was cooled to room temperature, dissolved in dichloromethane and the resulting solution was washed sequentially with 1M sodium hydroxide and water. The organic layer was then separated and dried over magnesium sulfate. The solvent was evaporated and the residue applied to a short column containing approximately 50 g of silica gel. The column was first eluted with dichloromethane to remove non-polar by-products, and subsequently eluted with ether to give 7-piperidino-2-(1,1-dimethylethyl)benz-4H-pyran-4-one (0.23 g, 14% yield) as a red oil. The structure of this compound was confirmed by mass spectroscopy and by $^1H$ and $^{13}C$ NMR spectroscopy.

EXAMPLE 15

Preparation of
7-piperidino-2-(1,1-dimethylethyl)-4-methylbenzpyrylium tetrafluoroborate This Example illustrates the preparation, by the reaction shown in FIG. 1, of the tetrafluoroborate salt of Formula II in which $R^1$ is a tertiary butyl group, $R^3$ is a piperidino group, $R^{14}$ is a methyl group, and $R^2$, $R^4$ and $R^5$ are each a hydrogen atom.

Methyl magnesium bromide (4 mL of a 3.0M solution in ether, 12 mmol) was added dropwise to a solution of 7-piperidino-2-(1,1-dimethylethyl)benz-4H-pyran-4-one (2.63 g, 9.25 mmol, prepared in Example 14 above) in dry tetrahydrofuran (10 mL) at 0° C. under nitrogen, and the solution was stirred at 25° C. for 17 hours, after which time tetrafluoroboric acid (4 mL of a 48% solution in water) was added, and the mixture was diluted with water (40 mL) and extracted with dichloromethane. The organic extracts were dried over sodium sulfate and concentrated in vacuo. The solid formed was triturated with ethyl acetate until it solidified and was then collected by vacuum filtration to give 7-piperidino-2-(1,1-dimethylethyl)-4-methylbenzpyrylium tetrafluoroborate (2.25 g, 66% yield) as an orange powder which melted at 172° C. with decomposition. The structure of this compound was confirmed by mass spectroscopy and by $^1H$ and $^{13}C$ NMR spectroscopy.

EXAMPLE 16

Preparation of
4-[5-[7-piperidino-2-[1,1-dimethylethyl]4H-benz[b]pyran-4-ylidene]penta-1,3-dienyl]-7-piperidino-2-(1,1-dimethylethyl]benz[b]pyrylium tetrafluoroborate This Example illustrates the preparation, by the reaction shown in FIG. 2, of the dye of Formula IB in which $R^1$ is a tertiary butyl group, $R^3$ is an piperidino group, and $R^2$, $R^4$, $R^5$ and $R^6$ are each a hydrogen atom.

Triethylamine (0.35 mL, 2.52 mmol) was added dropwise at 0° C. to a solution of 7-piperidino-2-(1,1-dimethylethyl)-4-methylbenzpyrylium tetrafluoroborate (914 mg, 2.5 mmol, prepared in Example 15 above) and 1,3,3-trimethoxyprop-1-ene (167 mg, 1.26 mmol) in acetic anhydride (4 mL) and the reaction mixture was warmed to room temperature and allowed to stand for 17 hours. After this time, the reaction mixture was poured into heptane to precipitate the crude dye. After removal of the solvents by decantation, the crude product was dissolved in dichloromethane and washed with water. The resultant solution was dried over sodium sulfate and concentrated in vacuo to give a crude product, which was further purified by medium pressure chromatography on silica gel with 5% methanol/dichloromethane as eluent to give the pure dye as a violet-red solid (300 mg, 35% yield). The dye had a strong infra-red absorption at 826 nm in dichloromethane solution, $\epsilon = 210,000$. The structure of this compound was confirmed by mass spectroscopy and by $^1$H and $^{13}$C NMR spectroscopy.

EXAMPLE 17

Preparation of 7-diethylamino-4-methyl-2-(1-methylpropyl)benzpyrylium tetrafluoroborate This Example illustrates the preparation, by the reaction shown in FIG. 3, of the tetrafluoroborate salt of Formula II in which $R^1$ is a secondary butyl group, $R^3$ is a diethylamino group, $R^{14}$ is a methyl group, and $R^2$, $R^4$ and $R^5$ are each a hydrogen atom.

A solution of 7-diethylamino-4-methylcoumarin (1 g, 4.3 mmol) in dry tetrahydrofuran (10 mL) was added dropwise to a solution of sec-butyl lithium (4.0 mL of a 1.3M solution in cyclohexane, 5.2 mmol) in dry tetrahydrofuran (50 mL) at 50° C. under nitrogen. The reaction mixture was then allowed to attain room temperature and stirred for 17 hours, after which time tetrafluoroboric acid (50 mL of a 25% solution in water) was added. The aqueous layer was separated and extracted with dichloromethane, and the combined organic layers were dried over sodium sulfate and evaporated. The crude salt, a red oil, was used directly in the next stage of the dye synthesis, as described in Example 18 below.

EXAMPLE 18

Preparation of 4-[5-[7-diethylamino-2-[1-methylpropyl]4H-benz[b]pyran-4-ylidene]penta-1,3-dienyl]-7-diethylamino-2-[1-methylpropyl]benz[b]pyrylium tetrafluoroborate This Example illustrates the preparation, by the method shown in FIG. 2, of the dye of Formula IB in Which $R^1$ is a secondary butyl group, $R^3$ is a diethylamino group, and $R^2$, $R^4$, $R^5$ and $R^6$ are each a hydrogen atom.

Triethylamine (500 mg, 4.95 mmol) was added dropwise to a solution of the red oil prepared in Example 17 above and 1,3,3-trimethoxy-1-propene (230 mg, 2.3 mmol) in acetic anhydride (10 mL) at room temperature under nitrogen. The reaction mixture was allowed to stand at room temperature for 4 hours, after which time hydrochloric acid (1M) was added. The resultant mixture was extracted with dichloromethane, and the organic layer was washed with a saturated solution of sodium bicarbonate and dried over sodium sulfate. The residue after removal of solvent was triturated with ether to give the dye as a black powder (135 mg, 4.7% yield over two steps). The dye had a strong infra-red absorption at 822 nm in dichloromethane solution, $\epsilon = 170,000$. The structure of this compound was confirmed by mass spectroscopy and by $^1$H and $^{13}$C NMR spectroscopy.

EXAMPLE 19

Preparation of 7-diethylamino-2-(1-methylethyl)-4-methylbenzpyrylium tetrafluoroborate This Example illustrates the preparation, by the reaction shown in FIG. 3, of the tetrafluoroborate salt of Formula II in which $R^1$ is an isopropyl group, $R^3$ is a diethylamino group, $R^{14}$ is a methyl group, and $R^2$, $R^4$ and $R^5$ are each a hydrogen atom.

Isopropyl magnesium bromide (70 mL of a 3M solution in ether, 0.21 mol) was added dropwise to a solution of 7-diethylamino-4-methylcoumarin (55.5 g, 0.24 mol) in dry toluene (700 mL) at 0° C. under nitrogen. The reaction mixture was then allowed to attain room temperature and stirred for 1 hour, after which time tetrafluoroboric acid (300 mL of a 25% solution in water) was added. The aqueous layer was separated, diluted with water (500 mL) and extracted with dichloromethane, and the combined organic layers were dried over sodium sulfate and evaporated. The crude salt, a dark purple slush, was used directly in the next stage of the dye synthesis, as described in Example 20 below.

EXAMPLE 20

Preparation of 4-[5-[7-diethylamino-2-[1-methylethyl]4H-benz[b]pyran-4-ylidene]penta-1,3-dienyl]-7-diethylamino-2-[1-methylethyl]benz[b]pyrylium tetrafluoroborate This Example illustrates the preparation, by the method shown in FIG. 2, of the dye of Formula IB in which $R^1$ is an isopropyl group, $R^3$ is a diethylamino group, and $R^2$, $R^4$, $R^5$ and $R^6$ are each a hydrogen atom.

Triethylamine (67 mL, 0.48 mol) was added dropwise to a solution of the purple slush prepared in Example 19 above and 1,3,3-trimethoxy-1-propene (31.5 g, 0.24 mol) in acetic anhydride (250 mL) with ice-bath cooling under nitrogen. The reaction mixture was allowed to stand at room temperature for 2 hours, after which time the solvent was removed in vacuo. The residue was triturated with ether and the crude product remaining was dissolved in dichloromethane. The resultant solution was washed successively with sufuric acid (1M), water and a saturated solution of sodium bicarbonate, dried over magnesium sulfate and concentrated in vacuo. The crude product was partially purified by medium-pressure chromatography on silica gel with $2 \geq 15\%$ methanol/dichloromethane as eluent. Fractions containing the dye were further purified by solution in tetrahydrofuran and reprecipitation with hexanes, to give the dye as a red-black powder (6.3 g, 9.4% yield over two steps, based upon the isopropyl magnesium bromide used as starting material in Example 19). The dye had a strong infra-red absorption at 822 nm in dichloromethane solution, $\epsilon = 200,000$. The structure of this compound was confirmed by mass spectroscopy and by $^1$H and $^{13}$C NMR spectroscopy.

EXAMPLE 21

Preparation of 7-dimethylamino-2-(1,1-dimethylethyl)benz-4H-pyran-4-one

This Example illustrates the preparation, by the reaction shown in FIG. 1, of the chromone of Formula V in which $R^1$ is a tertiary butyl group, $R^3$ is a dimethylamino group, and $R^2$, $R^4$ and $R^5$ are each a hydrogen atom.

3-Dimethylaminophenol (5.0 g, 36.5 mmol) and methyl 4,4-dimethyl-3-oxopentanoate (5.0 g, 31.6 mmol) were heated together under nitrogen at 200° C. for 2 hours. The reaction mixture was cooled to room temperature, dissolved in dichloromethane and applied to a short column containing approximately 200 g of silica gel. The column was first eluted with dichloromethane to remove non-polar by-products, and subsequently eluted with ether to give 7-dimethylamino-2-(1,1-dimethylethyl)benz-4H-pyran-4-one (1.16 g, 15% yield) as a tan solid, m.p. 114°–142° C. The structure of this compound was confirmed by mass spectroscopy and by $^1$H and $^{13}$C nuclear magnetic resonance (NMR) spectroscopy.

EXAMPLE 22

Preparation of 7-dimethylamino-2-(1,1-dimethylethyl)-4-methylbenzpyrylium tetrafluoroborate This Example illustrates the preparation, by the reaction shown in FIG. 1, of the tetrafluoroborate salt of Formula II in which $R^1$ is a tertiary butyl group, $R^3$ is a dimethylamino group, $R^{14}$ is a methyl group, and $R^2$, $R^4$ and $R^5$ are each a hydrogen atom.

Methyl magnesium bromide (0.6 mL of a 3.0M solution in ether, 1.8 mmol) was added dropwise to a solution of 7-dimethylamino-2-(1,1-dimethylethyl)benz-4H-pyran-4-one (0.20 g, 0.82 mmol, prepared in Example 21 above) in dry tetrahydrofuran (1 mL) at 0° C. under nitrogen. The reaction mixture was stirred at 25° C. for 5 hours and the solvent subsequently removed. Ethanol (2 mL) was added to the residue, followed by tetrafluoroboric acid (1 mL of a 50% solution in water), and precipitate formed. This precipitate was collected by vacuum filtration, washed with ethanol and dried in air to yield 7-dimethylamino-2-(1,1-dimethylethyl)-4-methylbenzpyrylium tetrafluoroborate (80 mg, 29% yield) as an orange solid melting at 242°–243° C. with decomposition. The structure of this compound was confirmed by mass spectroscopy and by $^1$H NMR spectroscopy.

This salt may be converted to the corresponding dyes of Formula I by the methods described above.

EXAMPLE 23

Preparation of 2-cyclohexyl-7-diethylaminobenz-4H-pyranone

This Example illustrates the preparation, by the reaction shown in FIG. 2, of the chromone of Formula V in which $R^1$ is a cyclohexyl group, $R^3$ is a diethylamino group, and $R^2$, $R^4$ and $R^5$ are each a hydrogen atom.

Piperidine (0.5 g) was added to a solution of 4-diethylamino-2-hydroxy-2'-(methylsulfonyl)acetophenone (2.69 g, 10 mmol, prepared as in Example 3, Part A above) and cyclohexanecarboxaldehyde (1.18 g, 10.5 mmol) in toluene (50 mL). The resultant solution was heated at reflux for 4 hours. After cooling to room temperature, the solvent was removed and the crude product was purified by sequential triturations with ice-cold hexanes and ice-cold ether. 2-Cyclohexyl-7-diethylaminobenz-4H-pyranone (1.96 g, 85% yield) was obtained as a yellow powder which melted at 109°–110° C. The structure of this compound was confirmed by mass spectroscopy and by $^1$H and $^{13}$C NMR spectroscopy.

EXAMPLE 24

Preparation of 2-cyclohexyl-7-diethylamino-4-methylbenzpyrylium tetrafluoroborate This Example illustrates the preparation, by the reaction shown in FIG. 1, of the tetrafluoroborate salt of Formula II in which $R^1$ is a cyclohexyl group, $R^3$ is a diethylamino group, $R^{14}$ is a methyl group, and $R^2$, $R^4$ and $R^5$ are each a hydrogen atom.

Methyl magnesium bromide (3.15 mL of a 3.0M solution in ether, 9.4 mmol) was added dropwise at 0° C. to a solution of 2-cyclohexyl-7-diethylaminobenz- 4H-pyranone (0.9 g, 3 mmol, prepared in Example 23 above) in dry tetrahydrofuran (50 mL) and the solution was allowed to stand at room temperature for about 17 hours. The reaction mixture was then poured into saturated ammonium chloride solution and the resultant mixture was extracted with dichloromethane. The organic layer was separated, washed with water, and then treated with tetrafluoroboric acid (10 mL of a 40% solution in water). After 1 hour, the solution was washed with water and dried over sodium sulfate. Removal of solvent yielded 2-cyclohexyl-7-diethylamino-4-methyl-benzpyrylium tetrafluoroborate (0.75 g, 67% yield) as a glassy solid. The structure of this compound was confirmed by mass spectroscopy and by $^1$H and $^{13}$C NMR spectroscopy.

EXAMPLE 25

Preparation of 4-[5-[7-diethylamino-2-cyclohexyl-4H-benz[b]pyran-4-ylidene]penta-1,3-dienyl]-7-diethylamino-2-cyclohexylbenz[b]pyrylium tetrafluoroborate This Example illustrates the preparation, by the method shown in FIG. 2, of the dye of Formula IB in which $R^1$ is a cyclohexyl group, $R^3$ is a diethylamino group, and $R^2$, $R^4$, $R^5$ and $R^6$ are each a hydrogen atom.

Triethylamine (0.18 mL, 1.29 mmol) was added dropwise to a solution of 2-cyclohexyl-7-diethylamino-4-methylbenzpyrylium tetrafluoroborate (0.43 g, 1.12 mmol, prepared in Example 24 above) and 1,3,3-trimethoxy-1-propene (0.1 g, 0.76 mmol) in acetic anhydride (4 mL) at 0° C. under nitrogen. The reaction mixture was stirred for 1 hour at 0° C., then at room temperature overnight. After this time, the reaction mixture was triturated with hexanes, dissolved in dichloromethane, washed with water, dried over sodium sulfate and concentrated under reduced pressure. The crude product was purified by preparative thin layer chromatography (TLC) on silica gel with 5% methanol/dichloromethane as eluent to give the dye as a purple-black powder (258 mg, 64% yield). The dye had a strong infra-red absorption at 827 nm in dichloromethane solution, $\epsilon = 309,000$. The structure of this compound was confirmed by mass spectroscopy and by $^1$H and $^{13}$C NMR spectroscopy.

EXAMPLE 26

Preparation of 7-diethylamino-2-[1,1-dimethyl-ethyl]benz-4H-pyran-4-thione

This Example illustrates the preparation, by the reaction shown in FIG. 4, of the thione of Formula XII in which $R^1$ is a tertiary butyl group, $R^3$ is a diethylamino group, and $R^2$, $R^4$ and $R^5$ are each a hydrogen atom.

Following a procedure analogous to that described in Walter, W. and Proll, T., Synthesis, 1979, 941, Lawesson's reagent (1.012 g, 2.5 mmol) was added in portions to a solution of 7-diethylamino-2-[1,1-dimethylethyl]benz-4H-pyran-4-one (1.37 g, 5.02 mmol, prepared in Example 4 above) in dry dimethoxyethane (5 mL). The reaction mixture was stirred at room temperature for one hour, then poured into water. The resultant mixture was extracted with dichloromethane, dried over sodium sulfate, and concentrated under reduced pressure. The crude material thus obtained was purified by flash chromatography on silica gel with 2% methanol/dichloromethane as eluent to give the slightly impure thioketone which was recrystallized from hexanes to give 848 mg (58% yield) of orange crystals which melted at 139°–140° C. The structure of this compound was confirmed by mass spectroscopy and by $^1H$ and $^{13}C$ NMR spectroscopy.

EXAMPLE 27

Preparation of 7-diethylamino-2-[1,1-dimethylethyl]-4-thiomethoxybenzpyrylium tetrafluoroborate This Example illustrates the preparation, by the reaction shown in FIG. 4, of the thiomethoxy tetrafluoroborate salt of Formula XIII in which $R^1$ is a tertiary butyl group, $R^3$ is a diethylamino group, and $R^2$, $R^4$ and $R^5$ are each a hydrogen atom.

A solution of 7-diethylamino-2-[1,1-dimethylethyl]-benz-4H-pyran-4-thione (0.70 g, 2.42 mmol, prepared in Example 26 above) in dichloromethane (10 mL) was added dropwise to a suspension of trimethyloxonium tetrafluoroborate (0.529 g, 3.58 mmol) in dichloromethane (10 mL) over 45 minutes at 0° C. After one hour of stirring at 0° C, the reaction mixture was allowed to warm to room temperature and then stirred overnight. The solvent was then removed under reduced pressure, and the residue was triturated with ethyl acetate to give the salt as a red powder (0.835 mg, 88% yield) which melted at 148°–150° C. The structure of this compound was confirmed by mass spectroscopy and by $^1H$ and $^{13}C$ NMR spectroscopy.

EXAMPLE 28

Preparation of 4-[1,1-dimethyl-5-methylcyclohex-4-en-3-ylidenemethyl]-2-[1,1-dimethylethyl]-7-diethylaminobenzpyrylium tetrafluoroborate This Example illustrates the preparation, by the reaction shown in FIG. 4, of the cyclohexenylidenemethyl tetrafluoroborate salt of Formula XIV in which $R^1$ is a tertiary butyl group, $R^3$ is a diethylamino group, $R^{14}$ is a methyl group, and $R^2$, $R^4$ and $R^5$ are each a hydrogen atom.

A solution of 7-diethylamino-2-[1,1-dimethylethyl]-4-methylbenzpyrylium tetrafluoroborate (5.003 g, 13.92 mmol, prepared in Example 5 above) in isophorone (7 mL, 46.72 mmol) was heated at reflux for 20 hours. The mixture was then poured into water, giving an oily residue, to which was added ethyl acetate. The ethyl acetate phase was extracted with water and dried under reduced pressure, then triturated with hexanes and further purified by flash chromatography with 5% methanol in dichloromethane as eluent to give the salt (3.816 g, 57% yield). The structure of this compound was confirmed by mass spectroscopy and by $^1H$ and $^{13}C$ NMR spectroscopy.

EXAMPLE 29

Preparation of 4-[[3-[2-[1,1-dimethylethyl]-7-diethylaminobenz[b]-4H-pyran-4-ylidene]methyl]-1,1-dimethylcyclohex-3-en-5-ylidenemethyl]-2-[1,1-dimethylethyl-7-diethylaminobenz[b]pyrylium tetrafluoroborate This Example illustrates the preparation, by the reaction shown in FIG. 4, of the dye of Formula 1D in which $R^1$ is a tertiary butyl group, $R^3$ is a diethylamino group, and $R^2$, $R^4$, $R^5$ and $R^6$ are each a hydrogen atom.

Triethylamine (0.05 mL) was added dropwise to a solution of 4-[1,1-dimethyl-5-methylcyclohex-4-en-3-ylidenemethyl]-2-[1,1-dimethylethyl]-7-diethylaminobenzpyrylium tetrafluoroborate (0.06 g, 0.22 mmol, prepared in Example 28 above) and 7-diethylamino-2-[1,1-dimethylethyl]-4-thiomethoxybenzpyrylium tetrafluoroborate (0.084 g, 0.21 mmol, prepared in Example 27 above) in dichloromethane (5 mL) at 0° C. and the reaction mixture was stirred for 18 hours at room temperature. The resultant crude product was purified by preparative TLC on silica gel with 5% methanol/dichloromethane as eluent to give the dye as a black amorphous powder (89.5 mg, 55 % yield), which melted at 119°–121° C. The dye had a strong infra-red absorption at 846 nm in dichloromethane solution, $\epsilon = 180,000$. The structure of this compound was confirmed by mass spectroscopy and by $^1H$ and $^{13}C$ NMR spectroscopy.

EXAMPLE 30

Preparation of glutaconic dialdehyde dianil monohydrochloride

This Example illustrates the preparation, by the reaction shown in FIG. 3, of the dianil of Formula X.

PART A

Preparation of N-(2,4-dinitrophenyl)pyridinium chloride (Formula IX)

1-Chloro-2,4-dinitrobenzene (10 g, 49.4 mmol) and pyridine (40 ml, 495 mmol) were mixed in a 100 ml round-bottom flask; the resultant solution turned orange and became very cold. The flask was then warmed to 30° C, by which time the solution was dark brown, and the solution was left to react overnight. The resulting solid was broken up, washed with ether and collected on a fritted glass funnel to yield 12.3 g of a pale pink, semicrystalline solid. This solid was dissolved in 120 ml of hot ethanol, and the resultant solution decolorized with charcoal and filtered. The crystals obtained were washed with a 1:1 v/v ethanol:ether mixture. A second crop of crystals was collected and combined with the first crop, to give an overall yield of 70% of theoretical.

PART B

Preparation of dianil monohydrochloride (For simplicity, the anil is shown in FIG. 3 in the form of the free base.)

The N-(2,4-dinitrophenyl)pyridinium chloride (1.03 g, 3.65 mmol) prepared in Part A was dissolved in hot ethanol (10 ml) in a round-bottom flask, aniline (0.65 ml, 7.1 mmol) was added and the mixture was refluxed for 5 minutes; after the first 2 minutes a purple precipitate formed. The reaction mixture was filtered hot and the purple solid obtained rinsed with cold ethanol and dried at 60° C. under vacuum for one hour to give 0.994 g of crude product. Since NMR analysis showed that the product was contaminated with 2,4-dinitroaniline byproduct, the product was dissolved in hot methanol (40 ml) and allowed to crystallize at room temperature for 1.5 hours. The overall yield was 34%.

EXAMPLE 31

Preparation of 4-[7-[7-diethylamino-2-1,1-dimethylethyl]4H-benz[b]-pyran-4-ylidene]hepta-1,3,5-trienyl]-7-diethylamino-2-[1,1-dimethylethyl]-benz[b]pyrylium tetrafluoroborate This Example illustrates the preparation, by the reaction shown in FIG. 3, of the dye of Formula 1C in which $R^1$ is a tertiary butyl group, $R^3$ is a diethylamino group, and $R^2$, $R^4$, $R^5$ and $R^6$ are each a hydrogen atom.

Triethylamine (0.4 mL, 2.86 mmol) was added dropwise to a stirred mixture of 7-diethylamino-2-[1,1-dimethylethyl]-4-methylbenzpyrylium tetrafluoroborate (1.006 g, 2.8 mmol, prepared in Example 5 above), glutaconic dialdehyde dianil monohydrochloride (0.4 g, 1.4 mmol, prepared in Example 30 above) and sodium acetate (0.235 g, 2.83 mmol) in acetic anhydride (8 mL) which had previously been stirred at room temperature for 10 minutes. The resultant mixture was stirred at room temperature for 2.5 hours, then triturated with hexanes. The oil remaining after trituration was dissolved in a minimum amount of dichloromethane and again triturated with hexanes. The oil remaining after this second trituration was dissolved in dichloromethane and the resultant solution was washed with water, dried over sodium sulfate and concentrated under reduced pressure to give the dye (1.055 g, 54.5 % yield) as a black powder which decomposed at 101°–103° C. The dye had a strong infra-red absorption at 947 nm in dichloromethane solution, $\epsilon = 284,000$. The structure of this compound was confirmed by mass spectroscopy and by $^1H$ and $^{13}C$ NMR spectroscopy.

EXAMPLE 32

Preparation of
4-[1-[2-chloro-3-[1-[7-diethylamino-2-[1,1-dimethylethyl]-4H-benz[b]pyran-4-ylidene]eth-2-ylidene]inden-1-yl]ethen-2-yl]-7-diethylamino-2-[1,1-dimethylethyl]-benz[b]pyrylium tetrafluoroborate This Example illustrates the preparation, by the reaction shown in FIG. 5, of the dye of Formula 1E in Which $R^1$ is a tertiary butyl group, $R^3$ is a diethylamino group, and $R^2$, $R^4$, $R^5$ and $R^6$ are each a hydrogen atom.

A mixture of 2-chloroinden-1,3-dicarboxaldehyde (0.33 g, 1.6 mmol, prepared by the procedure described in Collection Czech. Chem. Commun., 30(8), 2783-92 (1965) and Chem. Abstr., 63, 9882-3 (1965)), 7-diethylamino-2-[1,1-dimethylethyl]-4-methylbenzpyrylium tetrafluoroborate (1.16 g, 3.2 mmol, prepared in Example 5 above) and sodium acetate (0.10 g) in acetic anhydride (20 mL) was stirred for 2 hours at room temperature. The resultant mixture was triturated with hexane, and the solid which resulted was then purified by flash chromatography on silica gel with 2% methanol in dichloromethane as eluent to give the dye (0.35 g, 29% yield) as a copper solid. The dye had a strong infra-red absorption at 887 nm in dichloromethane solution, $\epsilon = 240,000$. The structure of this compound was confirmed by mass spectroscopy and by $^1H$ and 13C NMR spectroscopy.

EXAMPLE 33

Preparation of
2-[1,1-dimethylethyl]-4-methylbenzpyrylium tetrafluoroborate

This Example illustrates the preparation, by the reaction shown in FIG. 1, of the tetrafluoroborate salt of Formula II in which $R^1$ is a tertiary butyl group, $R^{14}$ is a methyl group, and $R^2$, $R^3$, $R^4$ and $R^5$ are each a hydrogen atom, starting from the corresponding chromone of Formula V.

Methyl magnesium bromide (2.4 mL of a 3.0M solution in ether, 7.2 mmol) was added dropwise at room temperature to a solution of 2-t-butylbenz-4H-pyranone (0.9 g, 4.5 mmol, see Bull. Chem. Soc. Japan, 46, 1839-1844 (1973)) in dry tetrahydrofuran (8 mL) and the solution was allowed to stand at room temperature for about 17 hours. The reaction mixture was then poured into stirred ice/water (50 mL) and the resultant mixture was acidified with tetrafluoroboric acid (5 mL of a 48% solution in water). After 15 minutes stirring, the mixture was extracted with dichloromethane (2×25 mL). The organic extracts were combined, dried over sodium sulfate and evaporated to give crude 2-[1,1-dimethylethyl]-4-methylbenzpyrylium tetrafluoroborate (1.05 g) as a brown solid.

This salt may be converted to the corresponding dyes of Formula I by the methods described above.

EXAMPLE 34

Preparation of
11-[1,1-dimethylethyl]-9-oxo-2,3,6,7-tetrahydro-1H,5H-[1]benzopyrano[6,7,8-ij]-quinolizine This Example illustrates the preparation, by the reaction shown in FIG. 1, of the chromone of Formula V in which $R^1$ is a tertiary butyl group, $R^5$ is a hydrogen atom, and $R^2$, $R^3$ and $R^4$ together form an $-N[-(CH_2)_3-]_2$ group in which the ends of the trimethylene groups remote from the nitrogen atom are joined to the benzpyrylium nucleus, so that the $-N[-(CH_2)_3-]_2$ group and the benzene ring of the benzpyrylium nucleus together form a julolidine ring system.

8-Hydroxyjulolidine (1.0 g, 5.29 mmol) and methyl 4,4-dimethyl-3-oxopentanoate (1.0 g, 6.32 mmol) were heated together under nitrogen at 200° C. for 4 hours, after which time more methyl 4,4-dimethyl-3-oxopentanoate (0.5 g, 3.16 mmol) was added and heating was continued for 2 hours. After cooling to room temperature, the reaction mixture was dissolved in dichloromethane and applied to a short column of silica gel (approx. 200 g). Elution with dichloromethane removed non-polar by-products, while subsequent elution with ether afforded 11-[1,1-dimethylethyl]-9-oxo-2,3,6,7-tetrahydro-1H,5H-[1]benzopyrano[6,7,8-ij]quinolizine (1.12 g, 71% yield) as a brown oil which solidified on standing. The structure of this compound was confirmed by mass spectroscopy and by $^1H$ and $^{13}C$ NMR spectroscopy.

EXAMPLE 35

Preparation of
11-[1,1-dimethylethyl]-9-methyl-2,3,6,7-tetrahydro-1H,5H-[1]benzopyrano[6,7,8-ij]quinolizinium tetrafluoroborate This Example illustrates the preparation, by the reaction shown in FIG. 1, of the tetrafluoroborate salt of Formula II in which $R^1$ is a tertiary butyl group, $R^5$ is a hydrogen atom, and $R^2$, $R^3$ and $R^4$ together form an $-N[-(CH_2)_3-]_2$ group in which the ends of the trimethylene groups remote from the nitrogen atom are joined to the benzpyrylium nucleus, so that the $-N[-(CH_2)_3-]_2$ group and the benzene ring of the benzpyrylium nucleus together form a julolidine ring system.

Methyl magnesium bromide (5.0 mL of a 3.0M solution in ether, 15 mmol) was added dropwise at 0° C. to a solution of 11-[1,1-dimethylethyl]-9-oxo-2,3,6,7-tetrahydro-1H,5H-[1]benzopyrano[6,7,8-ij]quinolizine (2.68 g, 9.03 mmol, prepared in Example 34 above) in dry tetrahydrofuran (10 mL) and the solution was allowed to stand at room temperature for about 17 hours. The reaction mixture was then cooled again to 0° C. and more methyl magnesium bromide (1 mL of a 3M solution in ether, 3 mmol) was added dropwise. The reaction mixture was allowed to attain room temperature and stirred for a further 8 hours, after which time the reaction mixture was poured into tetrafluoroboric acid (44 mL of a 4.4% solution in water) and the resultant mixture was extracted with dichloromethane. The organic phase was separated and dried over sodium sulfate. Removal of solvent, followed by trituration of the residue with ethyl acetate and filtration, gave 11-[1,1-dimethylethyl]-9-methyl-2,3,6,7-tetrahydro-1H,5H-[1]benzopyrano[6,7,8-ij]quinolizinium tetrafluoroborate (1.49 g, 44% yield) as a red solid which melted at 168°–170° C. The structure of this compound was confirmed by mass spectroscopy and by $^1$H and $^{13}$C NMR spectroscopy.

EXAMPLE 36

Preparation of
9-5-(11-[1,1-dimethylethyl]-2,3,6,7-tetrahydro-1H,5H--[1]benzopyrano[6,7,8-ij]quinolizin-9-ylidene]penta-1,3-dienyl]-11-[1,1-dimethylethyl]-2,3,6,7-tetrahydro-1H,5H-[b]benzopyrano[6,7,8-ij]quinolizinium tetrafluoroborate This Example illustrates the preparation, by the reaction shown in FIG. 2, of the dye of Formula 1B in which $R^1$ is a tertiary butyl group, $R^5$ is a hydrogen atom, and $R^2$, $R^3$ and $R^4$ together form an —N[—(CH$_2$)$_3$—]$_2$ group in which the ends of the trimethylene groups remote from the nitrogen atom are joined to the benzpyrylium nucleus, so that the —N[—(CH$_2$)$_3$—]$_2$ group and the benzene ring of the benzpyrylium nucleus together form a julolidine ring system.

Triethylamine (0.18 mL, 1.29 mmol) was added dropwise at 0° C. to a solution of 11-[1,1-dimethylethyl]-9-methyl-2,3,6,7-tetrahydro-1H,5H-[1]benzopyrano-[6,7,8-ij]quinolizinium tetrafluoroborate (502.4 mg, 1.31 mmol, prepared in Example 35 above) and 1,3,3-trimethoxyprop-1-ene (96 mg, 0.73 mmol) in acetic anhydride (2 mL). After standing for 1 hour at 0° C., the reaction mixture was warmed to room temperature and allowed to stand for a further 17 hours. After this time, the reaction mixture was poured into heptane to precipitate the crude dye. After removal of the solvents by decantation, the crude product was dissolved in dichloromethane and washed with water. The resultant solution was dried over magnesium sulfate and concentrated in vacuo to give the crude product, which was further purified by medium pressure chromatography on silica gel with 5% methanol/dichloromethane as eluent to give the pure dye as a violet-red solid (138.1 mg, 29.5% yield). The dye had a strong infra-red absorption at 855 nm in dichloromethane solution, $\epsilon=256,600$. The structure of this compound was confirmed by mass spectroscopy and by $^1$H and $^{13}$C NMR spectroscopy.

EXAMPLE 37

Preparation of
2-(6,6-dimethylbicyclo-[3.1.1]hept-2-en-2-yl)-7-diethylaminobenz-4H-pyranone This Example illustrates the preparation, by the reaction shown in FIG. 2, of the chromone of Formula V in which $R^1$ is a 6,6-dimethylbicyclo-[3.1.1]hept-2-en-2-yl group, $R^3$ is a diethylamino group, and $R^2$, $R^4$ and $R^5$ are each a hydrogen atom. Thus, in this chromone, the 2-substituent has a sp$^2$ carbon atom bonded directly to the benzpyrylium nucleus.

Piperidine (0.5 g) was added to a solution of 4-diethylamino-2-hydroxy-2'-(methylsulfonyl)-acetophenone (2.69 g, 10 mmol, prepared as in Example 3, Part A above) and (1R)-(−)-myrtenal (1.58 g, 10.5 mmol) in toluene (50 mL). The resultant solution was heated at reflux for 4 hours. After cooling the reaction mixture to room temperature, the solvent was removed and the crude product was purified by sequential triturations with hexanes and ice-cold ether. 2-(6,6-dimethylbicyclo[3.1.1]hept-2-en-2-yl)-7-diethylaminobenz-4H-pyranone (1.96 g, 46% yield) was obtained as a yellow powder. The structure of this compound was confirmed by mass spectroscopy and by $^1$H and $^{13}$C NMR spectroscopy.

EXAMPLE 38

Preparation of
2-(6,6-dimethylbicyclo-[3.1.1]hept2-en-2-yl)-7-diethylamino-4-methylbenzpyrylium tetrafluoroborate This Example illustrates the preparation, by the reaction shown in FIG. 1, of the tetrafluoroborate salt of Formula II in which $R^1$ is a 6,6-dimethylbicyclo-[3.1.1.]hept-2-en-2-yl group, $R^3$ is a diethylamino group, and $R^2$, $R^4$ and $R^5$ are each a hydrogen atom.

Methyl magnesium bromide (3.00 mL of a 3.0M solution in ether, 9.0 mmol) was added dropwise at 0° C. to a solution of 2-(6,6-dimethylbicyclo[3.1.1]hept-2-en-2-yl)-7-diethylaminobenz-4H-pyranone (0.8 g, 0.4 mmol, prepared in Example 37 above) in dry tetrahydrofuran (25 mL) and the solution was allowed to stand at room temperature for about 17 hours. The reaction mixture was then poured into tetrafluoroboric acid (55 mL of a 4.4% solution in water). The resultant mixture was extracted with dichloromethane, and the organic extracts were washed with water, dried over sodium sulfate and evaporated to give 2-(6,6-dimethylbicyclo[3.1.1]hept-2-en-2-yl)-7-diethylamino-4-methylbenzpyrylium tetrafluoroborate (0.94 g, 93% yield) as a glassy solid. The structure of this compound was confirmed by mass spectroscopy and by $^1$H and $^{13}$C NMR spectroscopy.

This salt may be converted to the corresponding dyes of Formula I by the methods described above.

EXAMPLE 39

Preparation of
2-[bicyclo[2.2.1]-hept-2-en-5-yl]-7-diethylaminobenz-4H-pyranone

This Example illustrates the preparation, by the reaction shown in FIG. 2, of the chromone of Formula V in which $R^1$ is a bicyclo[2.2.1]hept-2-en-5-yl group, $R^3$ is a diethylamino group, and $R^2$, $R^4$ and $R^5$ are each a hydrogen atom. Thus, in this chromone, the 2-substituent is ethylenically unsaturated but has a sp$^3$ carbon atom bonded directly to the benzpyrylium nucleus.

Piperidine (0.5 g) was added to a solution of 4-diethylamino-2-hydroxy-2'-(methylsulfonyl)-acetophenone (2.69 g, 10 mmol, prepared in Example 3, Part A above) and 5-norbornene-2-carboxaldehyde (1.28 g, 10.5 mmol) in toluene (50 mL). The resultant solution was heated at reflux for 4 hours. After cooling the solution to room temperature, the solvent was removed and the crude product was purified by sequential triturations with hexanes and ice-cold ether. 2-[bicyclo[2.2.1-]hept-2-en-5-yl]-7-diethylaminobenz-4H-pyranone (1.98 g, 61% yield) was obtained as a brown oil. The structure of this compound was confirmed by mass spectroscopy and by $^1$H and $^{13}$C NMR spectroscopy.

EXAMPLE 40

Preparation of
2-[bicyclo[2.2.1]hept-2-en-5-yl]-7-diethylamino-4-methylbenzpyrylium tetrafluoroborate This Example illustrates the preparation, by the reaction shown in FIG. 1, of the tetrafluoroborate salt of Formula II in which $R^1$ is a bicyclo[2.2.1]hept-2-en-5-yl group, $R^3$ is a diethylamino group, and $R^2$, $R^4$ and $R^5$ are each a hydrogen atom.

Methyl magnesium bromide (3.5 mL of a 3.0M solution in ether, 10.5 mmol) was added dropwise at 0° C. to a solution of 2-[bicyclo[2.2.1]hept-2-en-5-yl]-7-diethylaminobenz-4H-pyranone (0.87 g, 2.8 mmol, prepared in Example 39 above) in dry tetrahydrofuran (25 mL) and the solution was allowed to stand at room temperature for about 17 hours. The reaction mixture was then poured into tetrafluoroboric acid (55 mL of a 4.4% solution in water). The resultant mixture was extracted with dichloromethane, and the organic extracts were washed with water, dried over sodium sulfate and evaporated to give 2-[bicyclo[2.2.1]hept-2-en-5-yl]-7-diethylamino-4-methylbenzpyrylium tetrafluoroborate (0.75 g, 87% yield) as a brown oil. The structure of this compound was confirmed by mass spectroscopy and by $^1$H and $^{13}$C NMR spectroscopy.

This salt may be converted to the corresponding dyes of Formula I by the methods described above.

EXAMPLE 41

Preparation of
7-diethylamino-2-[1,1]-dimethylethyl]-4-ethylbenzpyrylium tetrafluoroborate This Example illustrates the preparation, by
shown in FIG. 1, of the tetrafluoroborate salt of Formula II in which $R^1$ is a tertiary butyl group, $R^3$ is a diethylamino group, $R^2$, $R^4$ and $R^5$ are each a hydrogen atom and $R^9$ is an ethyl group.

Ethyl magnesium bromide (17.0 mL of a 3M solution in ether, 51 mmol) was added dropwise at room temperature to a solution of 7-diethylamino-2-[1,1-dimethylethyl]-benz-4H-pyranone (11.2 g, 39.3 mmol, prepared in Example 1 above) in dry tetrahydrofuran (50 mL) and the solution was stirred at room temperature for 24 hours. The reaction mixture was poured into ice/water (400 mL), which was then acidified with tetrafluoroboric acid (50 mL of a 48% solution in water). The mixture so formed was extracted with dichloromethane and the organic phase was dried over sodium sulfate and evaporated. The residue was triturated with ether and filtered, to give 7-diethylamino-2-[1,1-dimethylethyl]-4-ethylbenzpyrylium tetrafluoroborate (11.8 g, 80% yield) as an orange solid. The structure of this compound was confirmed by mass spectroscopy and by $^1$H NMR spectroscopy.

This salt may be converted to the corresponding dyes of Formula I by the methods described above.

EXAMPLE 42

Preparation of
2-[1-adamantyl]-7-morpholinobenz-4H-pyran-4-one

This Example illustrates the preparation, by the reaction shown in FIG. 1, of the chromone of Formula V in which $R^1$ is an adamantyl group, $R^3$ is a morpholino group, and $R^2$, $R^4$ and $R^5$ are each a hydrogen atom.

3-Morpholinophenol (5.0 g, 27.9 mmol) and ethyl 3-adamantyl-3-oxo-butanoate (7.7 g, 30.7 mmol) were heated together under nitrogen for 6 hours at 195°–210° C. After cooling to room temperature, the reaction mixture was dissolved in dichloromethane and applied to a short column of silica gel (approx. 200 g). Elution with dichloromethane removed non-polar by-products, while subsequent elution with ether afforded a crude product which was re-chromatographed on silica gel to produce 2-[1-adamantyl]-7-morpholinobenz-4H-pyran-4-one as a brown solid (1.0 g, 10% yield). The structure of this compound was confirmed by mass spectroscopy and $^1$H NMR spectroscopy.

EXAMPLE 43

Preparation of
2-1-adamantyl]-4-methyl-7-moroholinobenzpyrylium tetrafluoroborate This Example illustrates the preparation, by the reaction shown in FIG. 1, of the tetrafluoroborate salt of Formula II in which $R^1$ is an adamantyl group, $R^3$ is a morpholino group, and $R^2$, $R^4$ and $R^5$ are each a hydrogen atom.

Methyl magnesium bromide (0.67 mL of a 3M solution in ether, 2 mmol) was added dropwise at room temperature to a solution of 2-[1-adamantyl]-7-morpholinobenz-4H-pyran-4-one (0.6 g, 1.6 mmol, prepared in Example 42 above) in dry tetrahydrofuran (15 mL) and the solution was stirred at room temperature for 24 hours. The reaction mixture was poured into ice/water (100 mL), which was then acidified with tetrafluoroboric acid (5 mL of a 48% solution in water). The mixture so formed was extracted with dichloromethane and the organic phase was dried over sodium sulfate and evaporated. The residue was triturated with ether and filtered to give 2-[1-adamantyl]-4-methyl-7-morpholinobenzpyrylium tetrafluoroborate (0.45 g, 66% yield) as a red solid. The structure of this compound was confirmed by mass spectroscopy and $^1$H NMR spectroscopy.

This salt may be converted to the corresponding dyes of Formula I by the methods described above.

EXAMPLE 44

Preparation of
2-[3,3-dimethylbut-1-en-1-yl]benz-4H-pyran-4-one

This Example illustrates the preparation of the chromone of Formula V, in which $R^1$ is a 3,3-dimethylbut-1-en-1-yl group (i.e., a 2-tertiary butyl vinyl group), and $R^2$, $R^3$, $R^4$ and $R^5$ are each a hydrogen atom, from the corresponding 2-methyl compound. Thus, in this chromone, the 2-substituent has an sp$^2$ carbon atom bonded directly to the benzpyrylium nucleus.

2-Methylbenz-4H-pyran (0.4 g, 2.5 mmol, prepared as described in Hirao et al., Synthesis, 1984, 1076) and trimethylacetaldehyde (0.5 g, 5.8 mmol) were sequentially added to a solution of sodium ethoxide in ethanol (25 mL of a 0.2M solution). The reaction mixture was heated at reflux for 3 hours, then poured into a saturated aqueous solution of ammonium chloride. The resultant mixture was extracted with ethyl acetate (3×25 mL), and the combined organic extracts were washed with a saturated sodium bicarbonate solution, dried over sodium sulfate and concentrated in vacuo. The residue, an amber oil, was purified by chromatography on silica gel with 9:1 hexanes/ethyl acetate as eluent to give 2-[3,3- dimethylbut-1-en-1-yl]benz-4H-pyran-4-one (0.12 g, 21% yield) as a yellow oil. The structure of this compound was confirmed by mass spectroscopy and by $^1$H and $^{13}$C NMR spectroscopy.

This chromone may be converted to the corresponding salt of Formula III and the corresponding dyes of Formula I by the methods described above.

EXAMPLE 45

Absorption of Dyes in Polymers

This Example illustrates the reduced tendency of the dyes of the present invention to develop absorptions at shorter wavelengths when dispersed in a polymer, as compared to similar dyes which bear a 2-phenyl substituent.

The dyes of the present invention used in these experiments were that prepared in Example 7, of Formula IB in which $R^1$ is a tertiary butyl group, $R^3$ is a diethylamino group, and $R^2$, $R^4$, $R^5$ and $R^6$ are each a hydrogen atom (hereinafter referred to as "Dye X") and that prepared in Example 25, of Formula IB in which $R^1$ is a cyclohexyl group, $R^3$ is a diethylamino group, and $R^2$, $R^4$, $R^5$ and $R^6$ are each a hydrogen atom (hereinafter referred to as "Dye Y"). The control dye was the 2-phenyl analogue of Dyes X and Y, hereinafter referred to as "Dye Z". The polymers used in these experiments were polyvinylbutyral (B-76 Butvar, supplied by Monsanto, and hereinafter referred to as "Polymer A"), poly(styrene/acrylonitrile) (B-71 SAN, supplied by Dow Chemical, and hereinafter referred to as "Polymer B"), poly(methyl methacrylate) (Elvacite 2021, supplied by DuPont, and hereinafter referred to as "Polymer C") and polyurethane (Estane 5712, supplied by B. F. Goodrich, and hereinafter referred to as "Polymer D").

The procedure used to disperse these dyes in polymers was as follows. The dye (0.5 mL of a 0.5% w/v solution in dichloromethane) was combined with the polymer (0.5 mL of a 10% w/w solution in methyl ethyl ketone) and the resulting solution was coated onto a transparent polyester base of 4 mil thickness using a #8 coating rod.

The absorption spectra of the dyes in the polymers exhibited two peaks in the near-infra-red, one similar to the absorption of the dye in solution (hereinafter designated "$A_1$" at wavelength $\lambda_1$), and a second, at shorter wavelength (hereinafter designated "$A_2$" at wavelength $\lambda_2$). The absorptions and wavelengths are set out in the Table below, together with the full width at half-height (referred to as simply "Width" in the Table, and measured in nanometers) of the principal peak; this is the shorter wavelength peak except where denoted by "(L)"; peak widths marked with an asterisk had to be estimated because of overlap between the two peaks.

TABLE

| Polymer | Dye | $\lambda_1$, nm | $\lambda_2$, nm | $A_1$ | $A_2$ | $A_1/A_2$ | Width |
|---|---|---|---|---|---|---|---|
| A | X | 821 | 736 | 1.061 | 0.433 | 2.45 | 77(L) |
|   | Y | 822 | 736 | 0.928 | 0.350 | 2.65 | 77(L) |
|   | Z | 861 | 750 | 0.254 | 0.439 | 0.58 | 150* |
| B | X | 828 | 748 | 1.150 | 0.417 | 2.76 | 72(L) |
|   | Y | 830 | 744 | 0.852 | 0.349 | 2.44 | 82(L) |
|   | Z | 873 | 763 | 0.264 | 0.378 | 0.70 | 140* |
| C | X | 816 | 723 | 0.911 | 0.580 | 1.57 | 88*(L) |
|   | Y | 814 | 722 | 0.526 | 0.381 | 1.38 | 94*(L) |
|   | Z | 862 | 700 | 0.186 | 0.485 | 0.38 | 160* |
| D | X | 821 | 730 | 0.779 | 0.432 | 1.80 | 88*(L) |
|   | Y | 824 | 730 | 0.367 | 0.261 | 1.41 | 108*(L) |
|   | Z | 864 | 752 | 0.139 | 0.225 | 0.62 | 220* |

From the data in the Table above, it will be seen that for Dyes X and Y of the present invention, the ratio $A_1/A_2$ was substantially greater than 1 in all the polymers tested, whereas for the 2-phenyl Dye Z, this ratio was substantially less than 1 in all the polymers tested.

Figure 7:
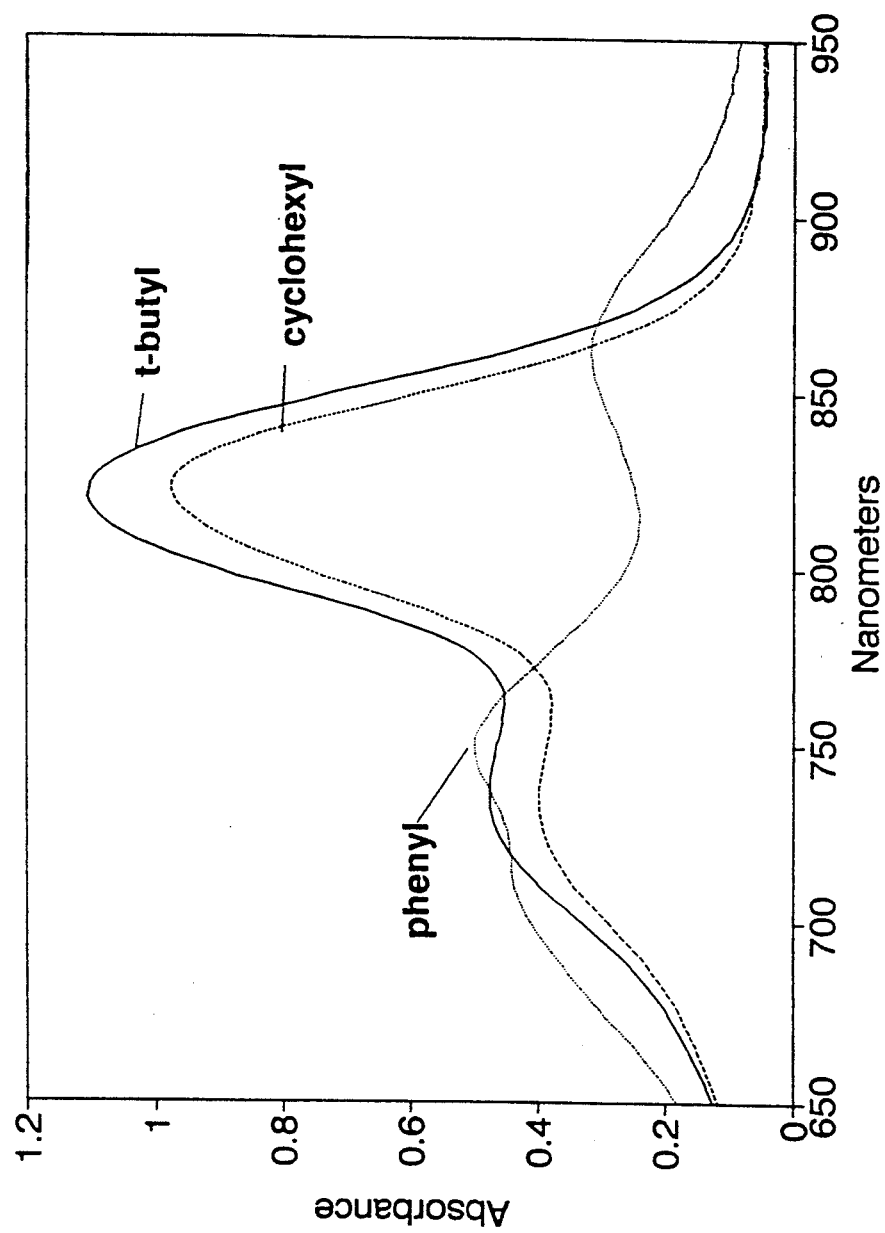
FIG. 7 shows the infra-red spectra produced in Example 45 below.

The spectra of the three dyes in Polymer A are shown in FIG. 7. From the data in FIG. 7, it will be seen that Dyes X and Y of the present invention display a single, well-defined major peak when present in a polymeric medium, with only a minor peak at shorter wavelength, whereas in control Dye Z the shorter wavelength absorption predominates, but the peaks are so broad that there is substantial absorption over a wide range of wavelengths.

For the reasons mentioned in the introductory part of this application, these results show that the dyes of the present invention are much more suitable for use as infra-red absorbers in imaging media where a narrow absorption range is desired than are the corresponding dyes in which the benzpyrylium nuclei bear 2-phenyl or other aromatic substituents.

EXAMPLE 46

Imaging medium containing dye of the invention

This Example illustrates the use of a dye of the present invention in a thermal imaging medium and process, as described above with reference to FIG. 6, except that, for experimental convenience, the imaging medium lacked the overcoat 16. The dye used in this Example was Dye X, as defined in Example 45 above.

A solution containing three parts by weight of Dye X and four parts by weight of a styrene/acrylonitrile copolymer (Dow SAN 880B, sold by Dow Chemical Corporation) in a 5:3:2 v/v methyl ethyl ketone/methyl propyl ketone/methyl amyl ketone mixture (this solution contained 6.98% solids by weight) was coated onto a corona-treated 1.5 mil poly(ethylene terephthalate) sheet (ICI 505, sold by ICI Americas, Inc) and dried to produce a sub-coat 14 having a thickness of approximately 0.6 μm.

A coating fluid for the colorant/binder layer 18 was prepared as follows. A pink pigment (9.0285 g of Hostaperm (Registered Trademark) Pink E pigment supplied by American Hoechst Corporation) and a carboxylated styrene/acrylic copolymer (Johnson Wax Joncryl 67, 4.5335 g of a 20% aqueous dispersion) were dispersed in water (46.5259 g), and the average particle size was then reduced to about 270 nm in an attritor to give a suspension of magenta particles. To 4.7367 g of this suspension were added water (1.5503 g) and poly(vinyl alcohol) (Air Products Vinol 540, 3.8227 g of a 3% aqueous solution), and the resulting fluid was coated on top of the sub-coat 14 produced above, and dried to produce a colorant/binder layer 18 having a thickness of about 1.0 micron.

To form the release layer 20, there was then coated a composition containing a polytetrafluoroethylene latex (Hoechst Hostaflon TF 5032, 1.0005 g of a 60% aqueous dispersion), silica (Nyacol CS 30, 2.0056 g of a 30% aqueous suspension), poly(vinyl alcohol) (Air Products Vinol 540, sold by Air Products, Inc., Allentown, Pa., 2.0134 g of a 3% aqueous solution), a fluorochemical surfactant (FC-120, available from Minnesota Mining and Manufacturing Corporation, Minneapolis, Minn., 0.0300 g of a 10% aqueous solution) and water (16.6304 g). The resultant coating was dried to produce a release layer 20 having a thickness of approximately 0.5 μm.

The resulting structure was laminated to a second sheet of poly(ethylene terephthalate) of thickness 4 mil which had been coated with a thermal adhesive (Whittaker AF-108) to a thickness of approximately 5 μm, this adhesive forming the layer 22.

The resultant imaging medium was exposed to infrared radiation from a GaAlAs semiconductor diode laser emitting at 819 nm and delivering 126 mW to the imaging medium. The laser output was focussed to a spot of about 120 square microns in area, and this spot was scanned across the medium at speeds of up to 7 m/s. Exposure was possible either through the 1.5 mil base (layer 12) or through the 4 mil base (layer 24). Greater sensitivity was achieved in the latter case. After exposure, the two sheets were peeled apart to reveal a pair of complementary images. Where the imaging medium had been exposed to the laser radiation, the colorant/binder layer 16 had adhered preferentially to the first sheet 12, and cohesive failure had occurred in the release layer 20. Where no exposure had occurred, the colorant/binder layer 16 had adhered preferentially to the second sheet 24, and failure of the structure had occurred between the sub-coat 14 and the colorant/binder layer 16.

What is claimed is:

1. A bis(benzpyrylium) polymethine dye wherein the dye moiety is of the formula:

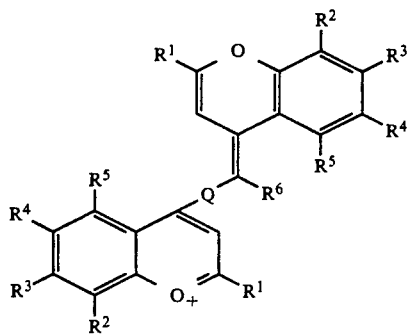

wherein:
Q is a group of formula $CR^6=CR^7-CR^8=CR^9$ or $CR^6=CR^7-CR^8=CR^9-CR^{10}=CR^{11}$;
each $R^1$ independently is an alkyl, alkenyl, alkynyl or alicyclic group;
each $R^2$ and $R^4$ independently is a hydrogen atom, an alkyl group containing not more than about 8 carbon atoms or a halogen atom;
each $R^5$ independently is a hydrogen atom, an alkyl group containing not more than about 8 carbon atoms, a halogen atom, or an alkoxy group containing not more than about 12 carbon atoms;
each $R^3$ independently is a hydrogen atom, an alkyl group containing not more than about 8 carbon atoms, an alkoxy group containing not more than about 12 carbon atoms, a morpholino or indolino group or a dialkylamino or dialkylphosphino group, subject to the proviso that when $R^3$ is a dialkylamino or dialkylphosphino group, the two alkyl groups thereof may form a polymethylene chain which, together with the nitrogen or phosphorus atom, forms a saturated ring.
each $R^6$ independently is a hydrogen atom or an alkyl group containing not more than about 6 carbon atoms;
each $R^7$, $R^8$, $R^9$, $R^{10}$ and $R^{11}$ independently is a hydrogen atom, an alkyl group containing not more than about 6 carbon atoms or a halogen atom.

2. A bis(benzpyrylium) polymethine dye according to claim 1 in which Q is a group of formula $CR^6=CR^7-CR^8=CR^9$, wherein $R^6$, $R^7$, $R^8$ and $R^9$ are as defined in claim 1.

3. A bis(benzpyrylium) polymethine dye according to claim 1 wherein each group $R^6$ is a hydrogen atom.

4. A bis(benzpyrylium) polymethine dye according to claim 1 wherein the carbon atom of each group $R^1$ which is directly attached to the benzpyrylium nucleus carries not more than one hydrogen atom.

5. A bis(benzpyrylium) polymethine dye according to claim 4 wherein the carbon atom of each group $R^1$ which is directly attached to the benzpyrylium nucleus does not have a hydrogen atom attached thereto.

6. A bis(benzpyrylium) polymethine dye according to claim 1 wherein each of the groups $R^1$ is an alkyl or cycloalkyl group.

7. A bis(benzpyrylium) polymethine dye according to claim 1 wherein each of the groups $R^1$ independently is an isopropyl, sec-butyl, tert-butyl, cyclohexyl, 2-tert-butylvinyl, 6,6-dimethylbicyclo[3.1.1]hept-2-en-2-yl, bicyclo[2.2.1]hept-2-en-5-yl or adamantyl group.

8. A bis(benzpyrylium) polymethine dye according to claim 1 wherein each of the groups $R^2$ and $R^4$ is a hydrogen atom.

9. A bis(benzpyrylium) polymethine dye according to claim 1 wherein each group $R^3$ is a dimethylamino, diethylamino, indolino, morpholino or piperidino group.

10. A bis(benzpyrylium) polymethine dye according to claim 1 wherein each of the groups $R^5$ independently is a hydrogen atom or a methoxy group.

11. A bis(benzpyrylium) polymethine dye according to claim 1 having a tetrafluoroborate, trifluoromethyl sulfonate, tetraphenyl borate or hexafluorophosphate anion.

12. A bis(benzpyrylium) polymethine dye according to claim 1 wherein:
 a. Q is a group of formula $CR^6=CR^7-CR^8=CR^9$, $R^1$ is a tertiary butyl group, $R^3$ is a diethylamino group, and $R^2$, $R^4$, $R^5$, $R^6$, $R^7$, $R^8$ and $R^9$ are each a hydrogen atom, namely 4-[5-[7-diethylamino-2-[1,1-dimethylethyl]4H-benz[b]pyran-4-ylidene]-penta-1,3-dienyl]-7-diethylamino-2-[1,1-dimethylethyl]benz[b]pyrylium salts;
 b. Q is a group of formula $CR^6=CR^7-CR^8=CR^9$, $R^1$ is a tertiary butyl group, $R^3$ is an indolino group, and $R^2$, $R^4$, $R^5$, $R^6$, $R^7$, $R^8$ and $R^9$ are each a hydrogen atom, namely 4-[5-[7-indolinyl-2-[1,1-dimethylethyl]4H-benz[b]pyran-4-ylidene]penta-1,3-dienyl]-7-indolinyl-2-[1,1-dimethylethyl]benz[b]pyrylium salts;
 c. Q is a group of formula $CR^6=CR^7-CR^8=CR^9$, $R^1$ is a tertiary butyl group, $R^3$ is an morpholino group, and $R^2$, $R^4$, $R^5$, $R^6$, $R^7$, $R^8$ and $R^9$ are each a hydrogen atom, namely 4-[5-[7-morpholino-2-[1,1-dimethylethyl]4H-benz[b]pyran-4-ylidene]-penta-1,3-dienyl]-7-morpholino-2-[1,1-dimethylethyl]benz[b]pyrylium salts;
 d. Q is a group of formula $CR^6=CR^7-CR^8=CR^9$, $R^1$ is a secondary butyl group, $R^3$ is a diethylamino group, and $R^2$, $R^4$, $R^5$, $R^6$, $R^7$, $R^8$ and $R^9$ are each a hydrogen atom, namely 4-[5-[7-diethylamino-2-[1-methylpropyl]4H-benz[b]pyran-4-ylidene]penta-1,3-dienyl]-7-diethylamino-2-[1-methylpropyl]-benz[b]pyrylium salts;

e. Q is a group of formula $CR^6=CR^7-CR^8=CR^9$, $R^1$ is an isopropyl butyl group, $R^3$ is a diethylamino group, and $R^2$, $R^4$, $R^5$, $R^6$, $R^7$, $R^8$ and $R^9$ are each a hydrogen atom, namely 4-[5-[7-diethylamino-2-[1-methylethyl]4H-benz[b]pyran-4-ylidene]penta-1,3-dienyl]-7-diethylamino-2-[1-methylethyl]-benz[b]pyrylium salts;

f. Q is a group of formula $CR^6=CR^7-CR^8=CR^9$, $R^1$ is a cyclohexyl group, $R^3$ is a diethylamino group, and $R^2$, $R^4$, $R^5$, $R^6$, $R^7$, $R^8$ and $R^9$ are each a hydrogen atom, namely 4-[5-[2-cyclohexyl-7-diethylamino-4H-benz[b]pyran-4-ylidene]penta-1,3-dienyl]-2-cyclohexyl-7-diethylamino-benz[b]pyrylium salts; and g. Q is a group of formula $CR^6=CR^7-CR^8=CR^9$, $R^1$ is a tertiary butyl group, $R^3$ is a diethylamino group, and $R^2$, $R^4$, $R^5$, $R^6$, $R^7$, $R^8$, $R^9$, $R^{10}$ and $R^{11}$ are each a hydrogen atom, namely 4-[7-[7-diethylamino-2-[1,1-dimethylethyl]4H-benz[b]pyran-4-ylidene]hepta-1,3,5-trienyl]-7-diethylamino-2-[1,1-dimethylethyl]-benz[b]pyrylium salts.

13. A bis(benzpyrylium) polymethine dye wherein the dye moiety is of the formula:

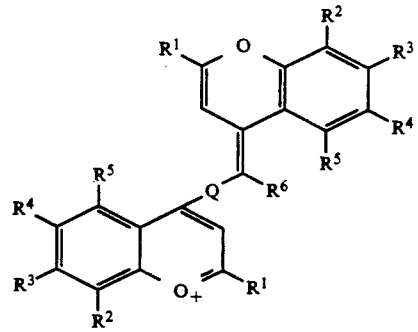

wherein:
Q is a group of formula $CR^6=CR^7-CR^8=CR^9$ or $CR^6aCR^7-CR^8CR^9-CR^{10}=Cr^{11}$;
each $R^1$ independently is an alkyl or cycloalkyl group;
each $R^2$ and $R^4$ independently is a hydrogen atom, an alkyl group containing not more than about 8 carbon atoms or a halogen atom;
each $R^5$ independently is a hydrogen atom, an alkyl group containing not more than about 8 carbon atoms, a halogen atom, or an alkoxy group containing not more than about 12 carbon atoms;
each $R^3$ independently is a hydrogen atom, an alkyl group containing not more than about 8 carbon atoms, an alkoxy group containing not more than about 12 carbon atoms, or a dialkylamino or dialkylphosphino group in which each of the alkyl groups contains not more than about 6 carbon atoms;
each $R^6$ independently is a hydrogen atom or an alkyl group containing not more than about 6 carbon atoms; and
each $R^7$, $R^8$, $R^9$, $R^{10}$ and $R^{11}$ independently is a hydrogen atom, an alkyl group containing not more than about 6 carbon atoms or a halogen atom.

* * * * *